(12) United States Patent
Truckai et al.

(10) Patent No.: US 6,905,497 B2
(45) Date of Patent: Jun. 14, 2005

(54) JAW STRUCTURE FOR ELECTROSURGICAL INSTRUMENT

(75) Inventors: Csaba Truckai, Arden, CT (US); James A. Baker, Palo Alto, CA (US); John H. Shadduck, Tiburon, CA (US)

(73) Assignee: Surgrx, Inc., Palo Alto, CA (US)

( * ) Notice: Subject to any disclaimer, the term of this patent is extended or adjusted under 35 U.S.C. 154(b) by 0 days.

(21) Appl. No.: 10/453,086

(22) Filed: May 31, 2003

(65) Prior Publication Data

US 2003/0199870 A1 Oct. 23, 2003

Related U.S. Application Data

(63) Continuation-in-part of application No. 10/079,728, filed on Feb. 19, 2002, and a continuation-in-part of application No. 10/032,867, filed on Oct. 22, 2001.
(60) Provisional application No. 60/384,429, filed on May 31, 2002.

(51) Int. Cl.[7] .............................................. A61B 18/12
(52) U.S. Cl. .......................................... 606/49; 606/51
(58) Field of Search ............................. 606/49–52, 205, 606/206, 208

(56) References Cited

U.S. PATENT DOCUMENTS

| 659,409 | A | 10/1900 | Mosher |
|---|---|---|---|
| 1,586,645 | A | 6/1926 | Bierman |
| 1,798,902 | A | 3/1931 | Raney |
| 1,881,250 | A | 10/1932 | Tomlinson |
| 2,031,682 | A | 2/1936 | Wappler et al. |
| 3,651,811 | A | 3/1972 | Hildebrandt et al. |
| 3,685,518 | A | 8/1972 | Beuerle et al. |
| 3,730,188 | A | 5/1973 | Ellman |
| 3,768,482 | A | 10/1973 | Shaw |
| 3,826,263 | A | 7/1974 | Cage et al. |

(Continued)

FOREIGN PATENT DOCUMENTS

| EP | 341 446 A2 | 4/1989 |
|---|---|---|
| EP | 517 244 B1 | 3/1996 |
| EP | 518 230 B1 | 5/1996 |
| FR | 2536924 A1 | 6/1984 |
| FR | 2647683 A1 | 12/1990 |
| GB | 2037167 A | 7/1980 |
| GB | 2066104 A | 7/1981 |
| GB | 2133290 A | 7/1984 |
| GB | 2161082 A | 1/1986 |
| SU | 342617 | 7/1972 |

(Continued)

OTHER PUBLICATIONS

Corson, S.L., "Two new laparoscopic instruments: Bipolar sterilizing forceps and uterine manipulator," *Medical Instumentation*, 11(1):7–8 (1977).

(Continued)

*Primary Examiner*—Roy D. Gibson
*Assistant Examiner*—Aaron Roane
(74) *Attorney, Agent, or Firm*—Townsend and Townsend and Crew LLP; Joel M. Harris, Patent Agent

(57) ABSTRACT

An electrosurgical medical device for creating thermal welds in engaged tissue that provides general grasping and dissecting functionality. In an exemplary embodiment, at least one jaw of the instrument defines a tissue engagement plane carrying electrosurgical energy delivery means. The jaw assembly, in one mode of operation, can be used for general grasping and dissecting purposes wherein the jaws close in a non-parallel manner so that the distalmost jaw tip only engage tissue with little movement of the actuator lever in the handle of the instrument. In another mode of operation, the jaw assembly closes close in a parallel manner under very high compression to enable tissue welding.

20 Claims, 22 Drawing Sheets

U.S. PATENT DOCUMENTS

| | | | |
|---|---|---|---|
| 4,092,986 A | 6/1978 | Schneiderman | |
| 4,198,957 A | 4/1980 | Cage et al. | |
| 4,219,025 A | 8/1980 | Johnson | |
| 4,231,371 A | 11/1980 | Lipp | |
| 4,232,676 A | 11/1980 | Herczog | |
| 4,271,838 A | 6/1981 | Lasner et al. | |
| 4,353,371 A | 10/1982 | Cosman | |
| 4,370,980 A | 2/1983 | Lottick | |
| 4,375,218 A | 3/1983 | DiGeronimo | |
| 4,492,231 A | 1/1985 | Auth | |
| 4,590,934 A | 5/1986 | Malis et al. | |
| 4,608,981 A | 9/1986 | Rothfuss et al. | |
| 4,633,874 A | 1/1987 | Chow et al. | |
| 4,655,216 A | 4/1987 | Tischer | |
| 4,671,274 A | 6/1987 | Sorochenko | |
| 4,691,703 A | 9/1987 | Auth et al. | |
| 4,763,669 A | 8/1988 | Jaeger | |
| 4,785,807 A | 11/1988 | Blanch | |
| 4,848,337 A | 7/1989 | Shaw et al. | |
| 4,850,353 A | 7/1989 | Stasz et al. | |
| 4,887,612 A | 12/1989 | Esser et al. | |
| 4,940,468 A | 7/1990 | Petillo | |
| 4,958,539 A | 9/1990 | Stasz et al. | |
| 4,969,885 A | 11/1990 | Farin | |
| 4,985,030 A | 1/1991 | Melzer et al. | |
| 5,009,656 A | 4/1991 | Reimels | |
| 5,057,106 A | 10/1991 | Kasevich et al. | |
| 5,057,107 A | 10/1991 | Parins et al. | |
| 5,085,659 A | 2/1992 | Rydell | |
| 5,104,025 A | 4/1992 | Main et al. | |
| 5,122,137 A | 6/1992 | Lennox | |
| 5,147,356 A | 9/1992 | Bhatta | |
| 5,147,357 A | 9/1992 | Rose et al. | |
| 5,151,102 A | 9/1992 | Kamiyama et al. | |
| 5,190,541 A | 3/1993 | Abele et al. | |
| 5,201,900 A | 4/1993 | Nardella | |
| 5,207,691 A | 5/1993 | Nardella | |
| 5,258,006 A | 11/1993 | Rydell et al. | |
| 5,267,998 A | 12/1993 | Hagen | |
| 5,269,780 A | 12/1993 | Roos | |
| 5,290,286 A | 3/1994 | Parins | |
| 5,306,280 A | 4/1994 | Bregen et al. | |
| 5,308,311 A | 5/1994 | Eggers et al. | |
| 5,324,289 A | 6/1994 | Eggers | |
| 5,336,221 A | 8/1994 | Anderson | |
| 5,360,428 A | 11/1994 | Hutchinson, Jr. | |
| 5,364,389 A | 11/1994 | Anderson | |
| 5,389,098 A | 2/1995 | Tsuruta et al. | |
| 5,403,312 A | 4/1995 | Yates et al. | |
| 5,417,687 A | 5/1995 | Nardella et al. | |
| 5,443,463 A | 8/1995 | Stern et al. | |
| 5,445,638 A | 8/1995 | Rydell et al. | |
| 5,451,224 A | 9/1995 | Goble et al. | |
| 5,458,598 A | 10/1995 | Feinberg et al. | |
| 5,480,397 A | 1/1996 | Eggers et al. | |
| 5,480,398 A | 1/1996 | Eggers | |
| 5,507,106 A | 4/1996 | Fox | |
| 5,531,744 A | 7/1996 | Nardella et al. | |
| 5,571,153 A | 11/1996 | Wallsten | |
| 5,573,535 A | 11/1996 | Viklund | |
| 5,593,406 A | 1/1997 | Eggers et al. | |
| 5,611,798 A | 3/1997 | Eggers | |
| 5,624,452 A | 4/1997 | Yates | |
| 5,674,220 A | 10/1997 | Fox et al. | |
| 5,693,051 A | 12/1997 | Schulze et al. | |
| 5,716,366 A | 2/1998 | Yates | |
| 5,735,848 A | 4/1998 | Yates et al. | |
| 5,755,717 A | 5/1998 | Yates et al. | |
| 5,766,166 A | 6/1998 | Hooven | |
| 5,776,130 A | 7/1998 | Buysse et al. | |
| 5,797,938 A | 8/1998 | Paraschal et al. | |
| 5,800,449 A | 9/1998 | Wales | |
| 5,807,392 A | 9/1998 | Eggers | |
| 5,833,690 A | 11/1998 | Yates et al. | |
| 5,911,719 A | 6/1999 | Eggers | |
| 5,947,984 A | 9/1999 | Whipple | |
| 6,019,758 A | 2/2000 | Slater | |
| 6,039,733 A | 3/2000 | Buysse et al. | |
| 6,074,389 A | 6/2000 | Levine et al. | |
| 6,086,586 A | 7/2000 | Hooven | |
| 6,113,598 A | 9/2000 | Baker | |
| 6,139,508 A | 10/2000 | Simpson et al. | |
| 6,152,923 A | 11/2000 | Ryan | |
| 6,162,220 A | 12/2000 | Nezhat | |
| 6,174,309 B1 | 1/2001 | Wrublewski et al. | |
| 6,176,857 B1 | 1/2001 | Ashley | |
| 6,179,834 B1 | 1/2001 | Buysse et al. | |
| 6,179,835 B1 | 1/2001 | Panescu et al. | |
| 6,179,837 B1 | 1/2001 | Hooven | |
| 6,187,003 B1 | 2/2001 | Buysse et al. | |
| 6,190,386 B1 | 2/2001 | Rydell | |
| 6,193,709 B1 | 2/2001 | Miyawaki et al. | |
| 6,270,497 B1 | 8/2001 | Sekino et al. | |
| 6,273,887 B1 | 8/2001 | Yamauchi et al. | |
| 6,277,117 B1 | 8/2001 | Tetzlaff et al. | |
| 6,296,640 B1 | 10/2001 | Wampler et al. | |
| 6,328,703 B1 | 12/2001 | Murakami | |
| 6,334,861 B1 | 1/2002 | Chandler et al. | |
| 6,350,264 B1 | 2/2002 | Hooven | |
| 6,352,536 B1 | 3/2002 | Buysse et al. | |
| 6,398,779 B1 | 6/2002 | Buysse et al. | |
| 6,409,725 B1 | 6/2002 | Khandkar et al. | |
| 6,451,018 B1 | 9/2002 | Lands et al. | |
| 6,458,128 B1 | 10/2002 | Schulze | |
| 6,458,130 B1 | 10/2002 | Frazier et al. | |
| 6,464,704 B2 | 10/2002 | Schmaltz | |
| 6,468,275 B1 | 10/2002 | Wampler et al. | |
| 6,500,176 B1 | 12/2002 | Truckai et al. | |
| 6,511,480 B1 | 1/2003 | Tetzlaff et al. | |
| 6,527,767 B2 | 3/2003 | Wang et al. | |
| 6,533,784 B2 | 3/2003 | Truckai et al. | |
| 6,554,829 B2 | 4/2003 | Schulze et al. | |
| 6,575,968 B1 | 6/2003 | Eggers et al. | |
| 6,585,735 B1 | 7/2003 | Frazier et al. | |
| 6,599,309 B1 * | 7/2003 | Gilman | 606/205 |
| 6,632,193 B1 | 10/2003 | Davison et al. | |
| 6,652,521 B2 | 11/2003 | Schulze | |
| 2002/0052599 A1 | 5/2002 | Goble | |
| 2002/0115997 A1 | 8/2002 | Truckai et al. | |
| 2002/0120266 A1 | 8/2002 | Truckai et al. | |
| 2002/0169392 A1 | 11/2002 | Truckai et al. | |
| 2002/0177848 A1 | 11/2002 | Truckai et al. | |
| 2003/0018327 A1 | 1/2003 | Truckai et al. | |
| 2003/0050635 A1 | 3/2003 | Truckai et al. | |
| 2003/0055417 A1 | 3/2003 | Truckai et al. | |
| 2003/0069579 A1 | 4/2003 | Truckai et al. | |
| 2003/0078573 A1 | 4/2003 | Truckai et al. | |

| | | |
|---|---|---|
| 2003/0078577 A1 | 4/2003 | Truckai et al. |
| 2003/0078578 A1 | 4/2003 | Truckai et al. |
| 2003/0114851 A1 | 6/2003 | Truckai et al. |
| 2003/0125727 A1 | 7/2003 | Truckai et al. |
| 2003/0139741 A1 | 7/2003 | Goble et al. |
| 2003/0144652 A1 | 7/2003 | Baker et al. |

FOREIGN PATENT DOCUMENTS

| | | |
|---|---|---|
| SU | 575103 | 10/1977 |
| WO | WO 93/08754 A1 | 5/1993 |
| WO | WO 94/24949 A1 | 11/1994 |
| WO | WO 94/24951 A1 | 11/1994 |

OTHER PUBLICATIONS

Burton, J.D.K., "New Inventions," *The Lancet*, pp. 650–651 (1959).

Nardella, P.C., "Radio Frequency Energy and Impedance Feedback," *Proc. SPIE, Catheter–Based Sensing and Imaging Technology*, 1068: 42–48 (1989).

Vallfors et al., "Automatically controlled bipolar electrocoagulation—'COA–COMP', " *Neurosurg Rev.*, 187–190 (1984).

\* cited by examiner

JAW STRUCTURE FOR ELECTROSURGICAL INSTRUMENT

CROSS-REFERENCE TO RELATED APPLICATIONS

This application claims benefit from Provisional U.S. Patent Application Ser. No. 60/384,429 filed May 31, 2002 having the same title, which application is incorporated herein by this reference. This application is a Continuation-In-Part of co-pending U.S. patent application Ser. No. 10/032,867 filed Oct. 22, 2001 titled Electrosurgical Jaw Structure for Controlled Energy Delivery, and U.S. patent application Ser. No. 10/079,728 filed Feb. 19, 2002 titles Electrosurgical Systems and Techniques for Sealing Tissue, both of which are incorporated herein by this reference.

BACKGROUND OF THE INVENTION

1. Field of the Invention

This invention relates to medical devices and techniques and more particularly relates to an electrosurgical jaw structure. The jaw assembly, in one mode of operation, can be used for general grasping and dissecting purposes wherein the jaws close in a non-parallel manner so that the distalmost jaw tips only engage tissue with little movement of the actuator lever in the handle of the instrument. In another mode of operation, the jaw assembly closes in a parallel manner under very high compression to enable tissue welding.

2. Description of the Related Art

In various open and laparoscopic surgeries, it is necessary to coagulate, seal or weld tissues. One preferred means of tissue-sealing relies upon the application of electrical energy to captured tissue to cause thermal effects therein for sealing purposes. Various mono-polar and bi-polar radiofrequency (Rf) jaw structures have been developed for such purposes. In a typical bi-polar jaw arrangement, each jaw face comprises an electrode and Rf current flows across the captured tissue between the first and second polarity electrodes in the opposing jaws. While such bi-polar jaws can adequately seal or weld tissue volumes that have a small cross-section, such bi-polar instruments often are ineffective in sealing or welding many types of tissues, such as anatomic structures having walls with irregular or thick fibrous content, bundles of disparate anatomic structures, substantially thick anatomic structures, or tissues with thick fascia layers such as large diameter blood vessels.

Prior art Rf jaws that engage opposing sides of a tissue volume typically cannot cause uniform thermal effects in the tissue, whether the captured tissue is thin or substantially thick. As Rf energy density in tissue increases, the tissue surface becomes desiccated and resistant to additional ohmic heating. Localized tissue desiccation and charring can occur almost instantly as tissue impedance rises, which then can result in a non-uniform seal in the tissue. The typical prior art Rf jaws can cause further undesirable effects by propagating Rf density laterally from the engaged tissue to cause unwanted collateral thermal damage.

What is needed is an instrument with a jaw structure that can apply Rf energy to tissue in new modalities: (i) to weld or seal tissue volumes that have substantial fascia layers or tissues that are non-uniform in hydration, density and collagenous content; (ii) to weld a targeted tissue region while substantially preventing thermal damage in regions lateral to the targeted tissue; and (iii) to weld a bundle of disparate anatomic structures.

SUMMARY OF THE INVENTION

The principal objective of the present invention is to provide an electrosurgical jaw structure and Rf energy control system that is capable of precisely modulating energy to engaged tissue over a selected time interval to accomplish tissue welding. As background, the biological mechanisms underlying tissue fusion or welding by means of thermal effects are not fully understood. In general, the application of Rf energy to a captured tissue volume causes ohmic heating (alternatively described as active Rf heating herein) of the tissue to thereby at least partially denature proteins in the tissue. By ohmic heating, it is meant that the active Rf current flow within tissue between electrodes causes resistive heating of conductive compositions (e.g., water) in the tissue.

One objective of the invention is to denature tissue proteins, including collagen, into a proteinaceous amalgam that intermixes and fuses together as the proteins renature. As the treated region heals over time, the so-called weld is reabsorbed by the body's wound healing process. A more particular objective of the invention is to provide a system that (i) instantly and automatically modulates ohmic heating of tissue to maintain a selected temperature in the tissue, and (ii) to instantly and automatically modulate total energy application between active Rf heating (resulting from tissue's resistance to current flow therethrough) and conductive heating of tissue cause by the thermal capacity of the jaw components.

In one exemplary embodiment, a jaw of the instrument defines a tissue engagement plane that engages the tissue targeted for welding. The engagement plane carries first and second surface portions that comprise, respectively an electrical conductor and a variable resistive body or positive temperature coefficient (PTC) material having a resistance that increases at higher temperatures. A variable resistive body of a dope polymer or ceramic can be engineered to exhibit a positively sloped curve of temperature-resistance over a temperature range of about 37° C. to 100° C. The region at the higher end of such a temperature range brackets a targeted "thermal treatment range" at which tissue can be effectively welded. The selected resistance of the variable resistive body at the upper end of the temperature range will substantially terminate current flow therethrough.

In operation, it can be understood that the engagement plane will apply active Rf energy (ohmic heating within) to the engaged tissue until the point in time that the variable resistive body is heated to exceed the maximum of the thermal treatment range. Thereafter, Rf current flow from the engagement surface will be lessened—depending on the relative surface areas of the first and second surface portions. This instant and automatic reduction of Rf energy application can be relied on to prevent any substantial dehydration of tissue proximate to the engagement plane. By thus maintaining an optimal level of moisture around the engagement plane, the working end can more effectively apply energy to the tissue—and provide a weld thicker tissues with limited collateral thermal effects.

The jaw assembly corresponding to the invention further provides a suitable cross-section and mass for providing a substantial heat capacity. Thus, when the variable resistive body is elevated in temperature to the selected thermal treatment range, the retained heat of the variable resistive matrix volume can effectively conduct thermal energy to the engaged tissue volume. Thus, in operation, the working end can automatically modulate the application of energy to tissue between active Rf heating and passive conductive heating of the targeted tissue to maintain the targeted temperature level.

The jaw assembly corresponding to the invention is moved between an open position and closed position about an engagement plane by the positive engagement of the proximally-facing cams and distally-facing cams carried by a reciprocating member. Thus, the jaw assembly can be used effectively to dissect tissue by inserting the tip of the jaw assembly into a tissue plane and then opening the jaws with substantial from to thus separate and dissect the tissue. This is not possible with many jaw assemblies of surgical instrumemts that use springs to move the jaws toward an open position.

Additional objects and advantages of the invention will be apparent from the following description, the accompanying drawings and the appended claims.

DETAILED DESCRIPTION OF THE INVENTION

Figure 1:
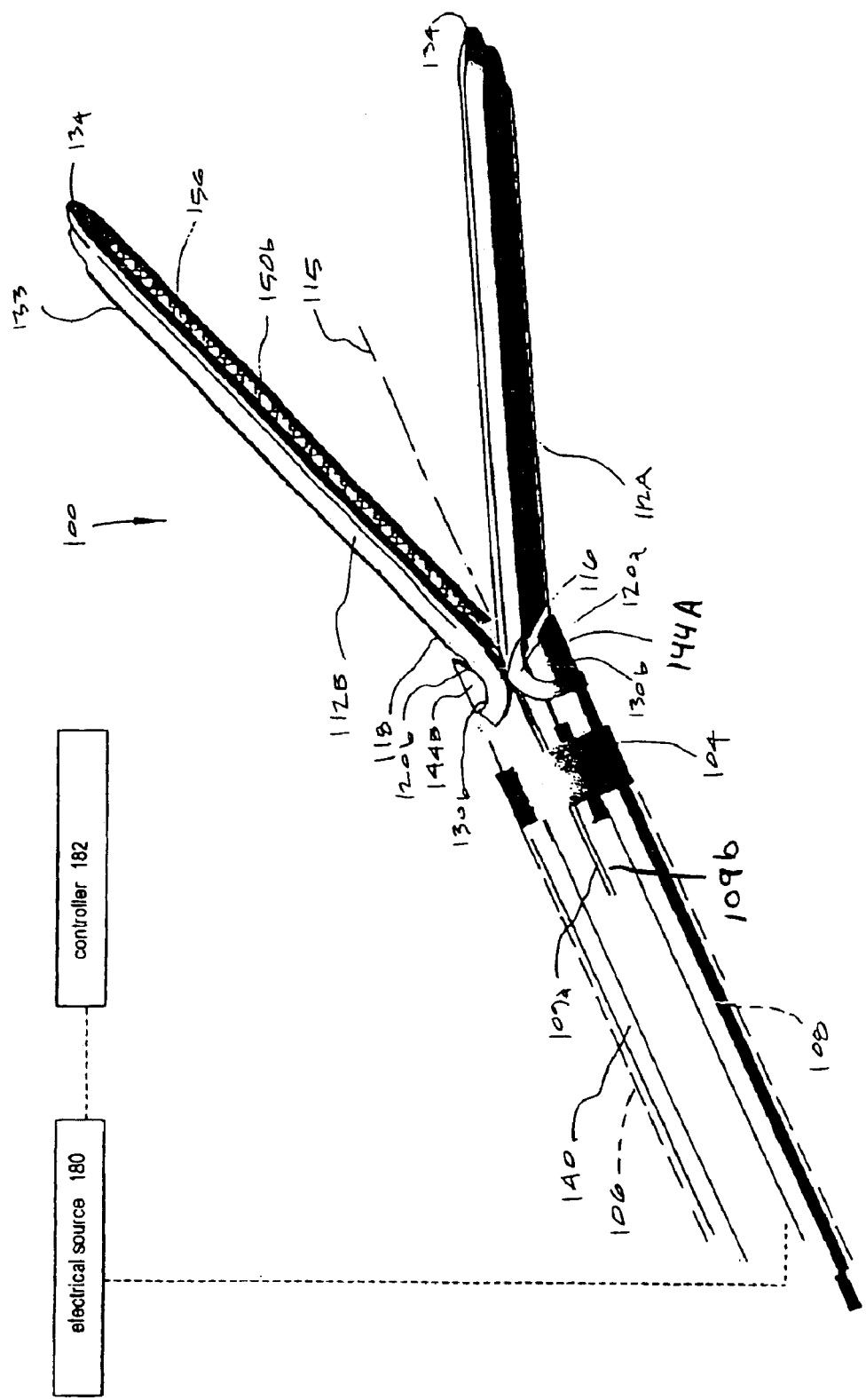
FIG. 1 is a perspective view of a Type "A" introducer and electrosurgical jaw assembly illustrating the first and second cam surfaces of the jaws that are adapted for positive engagement with a reciprocating member for both closing and opening the jaws.
Figure 2:
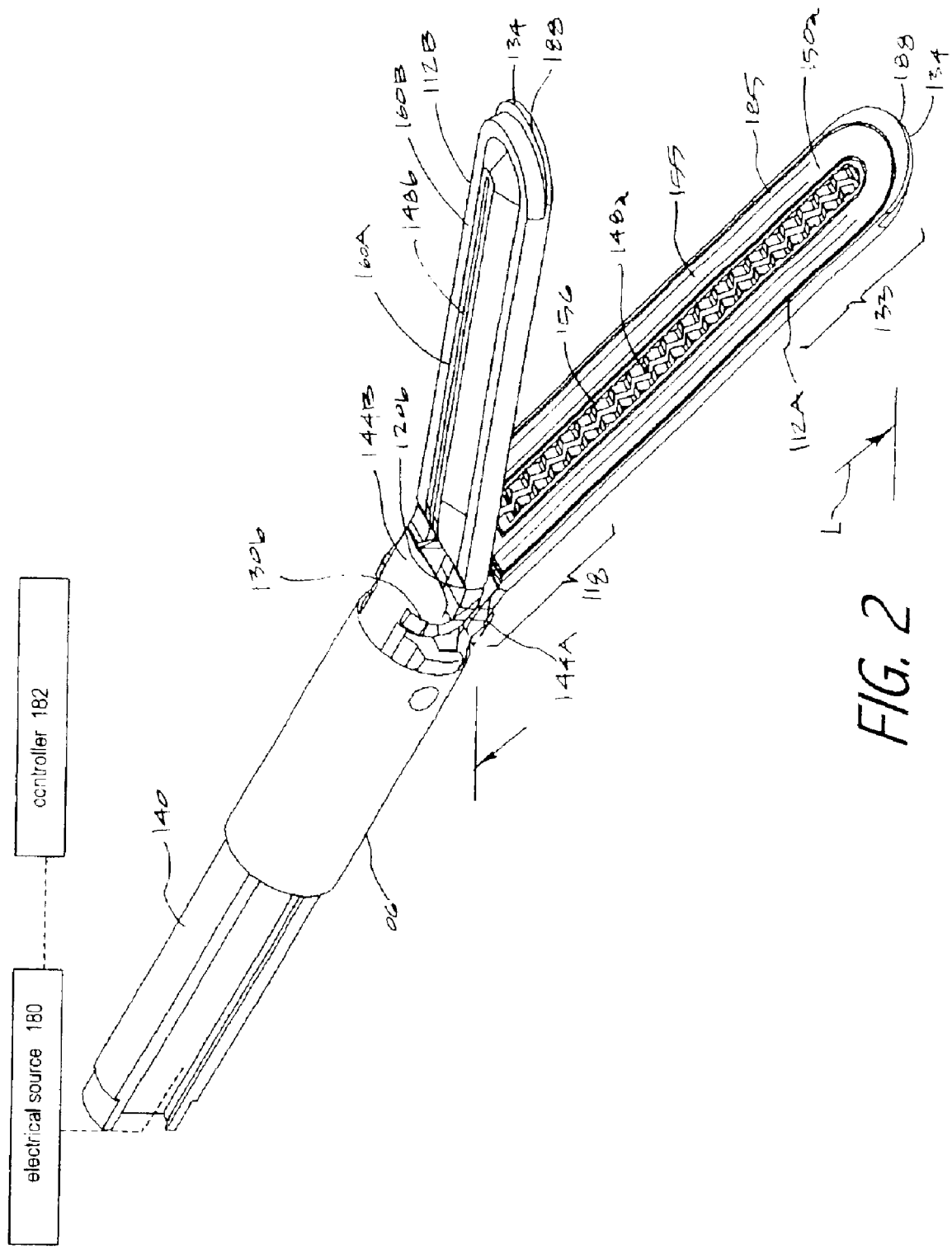
FIG. 2 is another perspective view of the Type "A" jaw assembly of FIG. 1 illustrating the engagement surfaces of the jaws.

1. Type "A" jaw assembly. An exemplary Type "A" jaw assembly 100 of a surgical grasping instrument is illustrated in FIGS. 1 and 2 which is adapted for transecting captured tissue and contemporaneous welding of the captured tissue with Rf energy delivery. The jaw assembly 100 is carried at the distal end 104 of an introducer sleeve member 106 that can be rigid, articulatable or deflectable in any suitable diameter. For example, the introducer sleeve portion 106 can have a diameter ranging from about 2 mm., to 20 mm. to cooperate with cannulae in endoscopic surgeries or for use in open surgical procedures. The introducer portion 106 extends from a proximal handle (not shown). The handle can be any type of pistol-grip or other type of handle known in the art that carries actuator levers, triggers or sliders for actuating the jaws as will be disclosed below, and need not be described in further detail. The introducer sleeve portion 106 has a bore 108 extending therethrough for carrying actuator mechanisms for actuating the jaws and for carrying electrical leads 109a–109b for the electrosurgical components of the working end.

Figure 9:
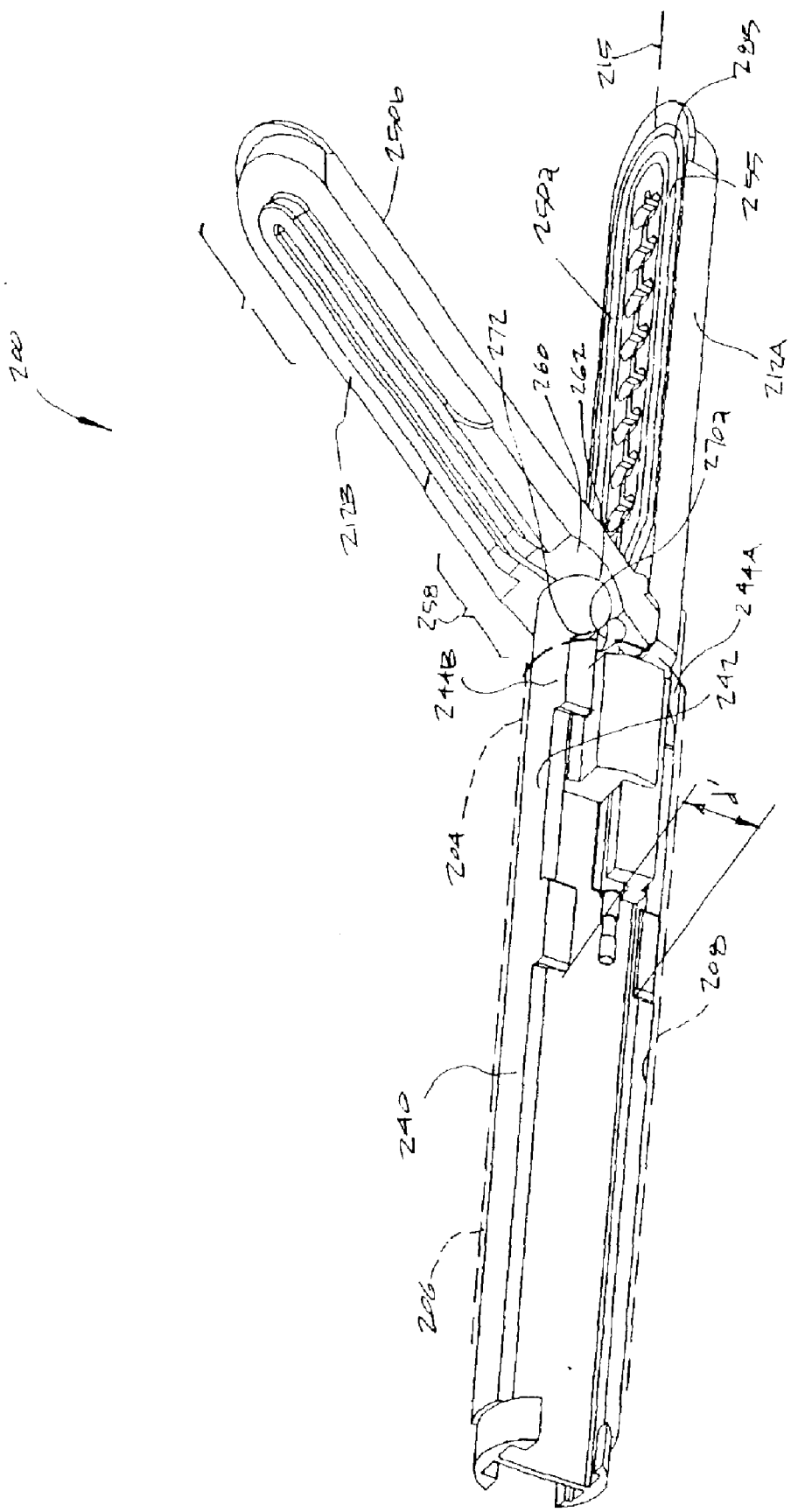
FIG. 9 is a perspective view of a Type "B" electrosurgical working end with the jaws in an open position showing first and second cam surfaces carried on a single rotatable jaw.
Figure 10:
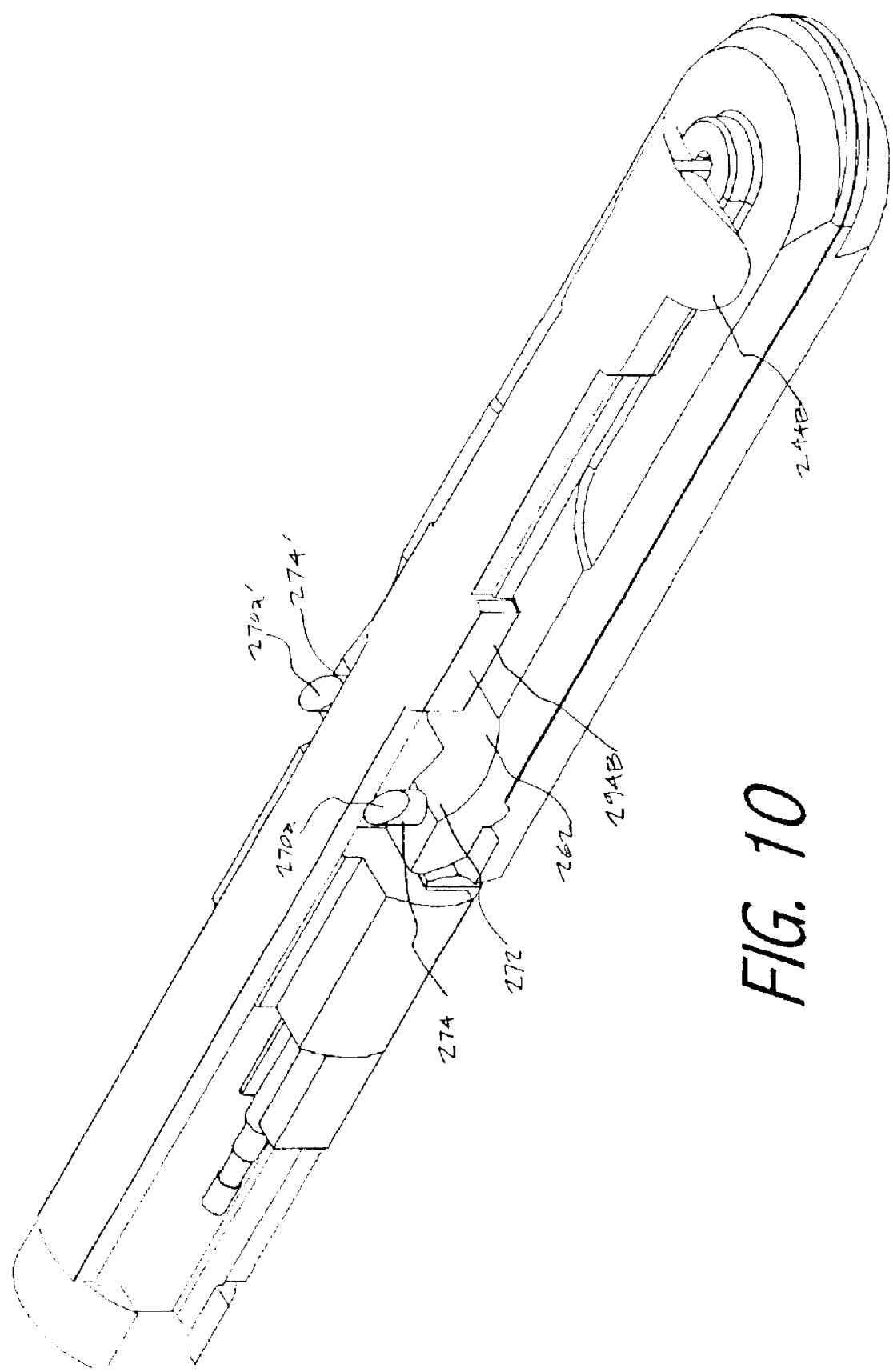
FIG. 10 is a perspective view of the Type "B" working end of FIG. 9 with the jaws in a closed position again showing the first and second cam surfaces of the single rotatable jaw.

As can be seen in FIGS. 1 and 2, the jaw assembly 100 has first (lower) jaw element 112A and second (upper) jaw element 112B that are adapted to close or approximate about axis 115. The jaw elements may both be moveable or a single jaw may rotate to provide the open and closed positions. In the exemplary embodiment of FIGS. 1 and 2, both the lower and upper jaws 112A–112B are moveable relative to a rolling pivot location 116 defined further below. Another exemplary embodiment with a fixed lower jaw portion 112A and rotatable upper jaw 112B is shown in FIGS. 9 and 10.

Of particular interest, the opening-closing mechanism of the jaw assembly 100 corresponding to the invention operates on the basis of cam mechanisms that provide a positive engagement of camming surfaces (i) for moving the jaw assembly to the (second) closed position to engage tissue under very high compressive forces, and (ii) for moving the jaws toward the (first) open position to apply substantially high opening forces for "dissecting" tissue. This important feature allows the surgeon to insert the tip of the closed jaws into a dissectable tissue plane—and thereafter open the jaws to apply such dissecting forces against the tissues (see FIG. 7A).

Referring to FIGS. 1 and 2, the lower and upper jaws 112A–112B have a first end 118, in the open position, that defines first (proximally-facing) arcuate outer surface portions indicated at 120a and 120b that are engaged by a first surface portions 122a and 122b of reciprocatable member 140 that is adapted to slide over the jaw elements to thereby move the jaws toward closed position. The first end portion 118 of the lower and upper jaws, in the open position, further defines second (distally-facing) arcuate surface portions indicated at 130a and 130b that are engaged by second surface portions 132a and 132b of the reciprocatable member 140 for moving the jaw elements to the open position. The distal (second) end region 133 of the paired jaws is rounded with a lip 134 that can serve as an electrode for surface coagulation as will be described below.

In this embodiment of FIGS. 1 and 2, the reciprocating member 140 (see FIGS. 3 and 4) is actuatable from the handle of the instrument by any suitable mechanism, such as a lever arm, as is known in the art that is coupled to a proximal end 141 of member 140. The proximal end 141 and medial portion 141' of member 140 are dimensioned to reciprocate within bore 108 of introducer sleeve 106. The distal portion 142 of reciprocating member 140 carries first (lower) and second (upper) laterally-extending flanges or shoulder elements 144A and 144B that are coupled by intermediate transverse element 145. The transverse element 145 further is adapted to transect tissue captured between the jaws with a leading edge 146 (FIG. 3) that can be a blade or a cutting electrode. The transverse element 145 is adapted to slide within a channels 148a and 148b in the paired first and second jaws. As can be seen best in FIGS. 3 and 4, the laterally-extending shoulder elements 144A and 144B define the surfaces 122a, 122b, 132a and 132b that slidably engage the arcuate cam surfaces of the jaws and that apply high compressive forces to the jaws in the closed position (FIG. 7B).

Referring back to FIGS. 1 and 2, the first and second jaws 112A and 112B define tissue-engaging surfaces or planes 150a and 150b that contact and deliver energy to engaged tissues, in part, from an Rf electrode arrangement therein indicated at 155. The jaws can have any suitable length with teeth or serrations 156 in any location for gripping tissue. The embodiment of FIGS. 1 and 2 depicts such serrations 156 at an inner portion of the jaws along channels 148a and 148b thus leaving engagement planes 150a and 150b laterally outward of the tissue-gripping elements. In the embodiments described below, the engagement planes 150a and 150b and electrode(s) 155 generally are shown with a non-serrated surface for clarity of explanation, but such engagement planes and electrodes themselves can be any non-smooth gripping surface. The axial length of jaws 112A and 112B indicated at L can be any suitable length depending on the anatomic structure targeted for transection and sealing and typically will range from about 10 mm. to 50 mm. The jaw assembly can apply very high compression over much longer lengths, for example up to about 200 mm. for example resecting and sealing organs such as a lung or liver. The scope of the invention also covers jaw assemblies for an instrument used in micro-surgeries wherein the jaw length can be as little as about 5.0 mm.

In the exemplary embodiment of FIGS. 1 and 2, the engagement plane 150a of the lower jaw 112A is adapted to deliver energy to tissue, and the tissue-contacting surface 150b of upper jaw 112B can be electrosurgically active or passive as will be described below. Alternatively, the engagement surfaces of the jaws can carry any of the electrode arrangements disclosed in co-pending U.S. patent application Ser. No. 09/032,867 filed Oct. 22, 2001 titled Electrosurgical Jaw Structure for Controlled Energy Delivery and Ser. No. 10/308,362 filed Dec. 3, 2002 titled Electrosurgical Jaw Structure for Controlled Energy Delivery both of which are incorporated herein by reference.

Figure 3:
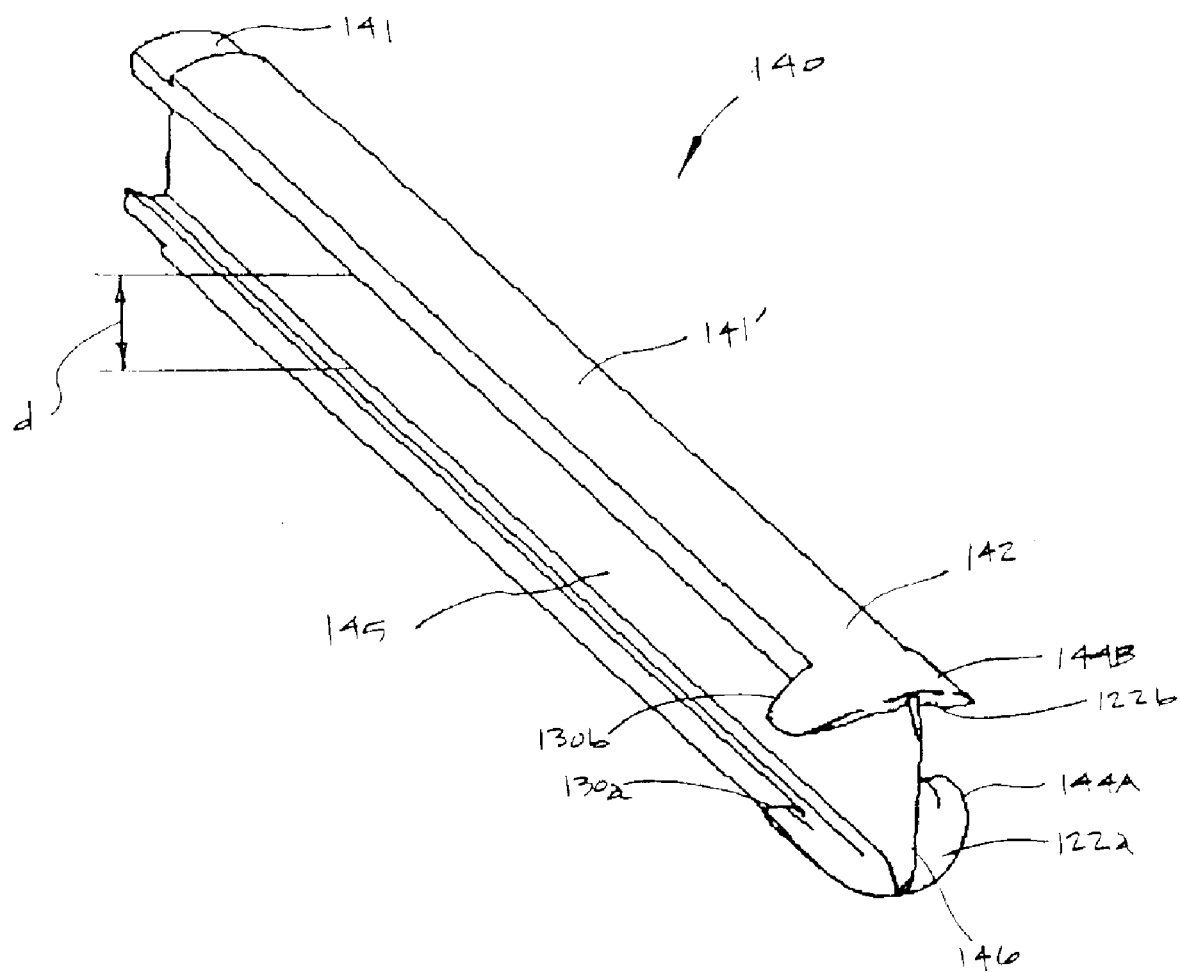
FIG. 3 is a perspective view of the reciprocatable extension member of the Type "A" electrosurgical working end of FIGS. 1–2 shown de-mated from the working end.
Figure 4:
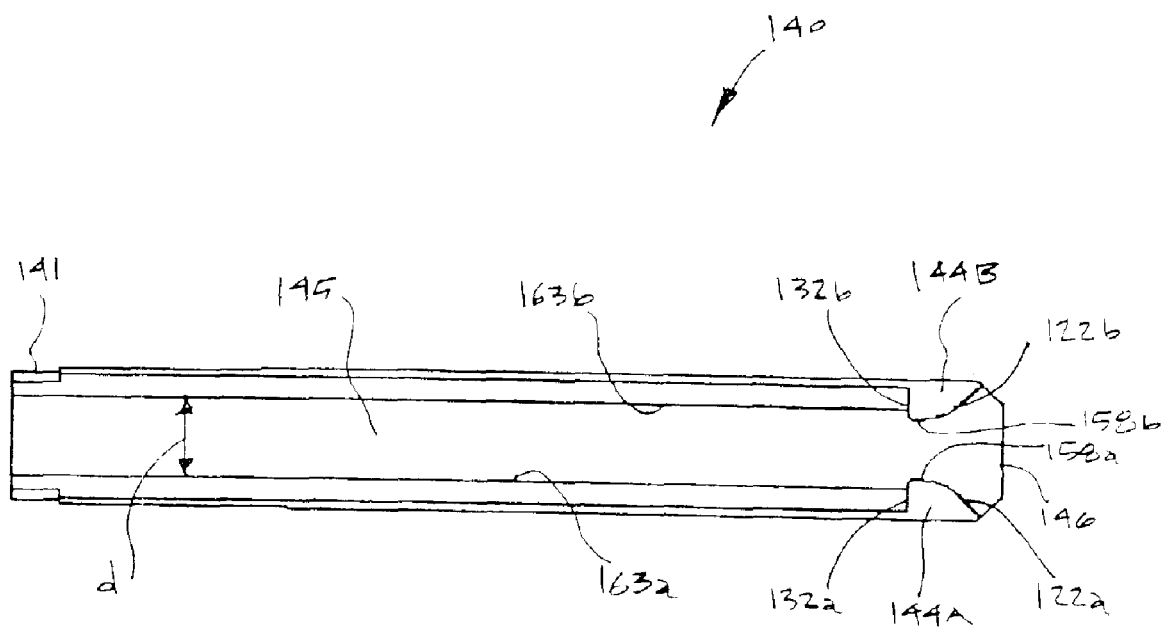
FIG. 4 is a plan view of the de-mated reciprocatable member of FIG. 3 showing the first and second cam surfaces thereof.
Figure 5A:
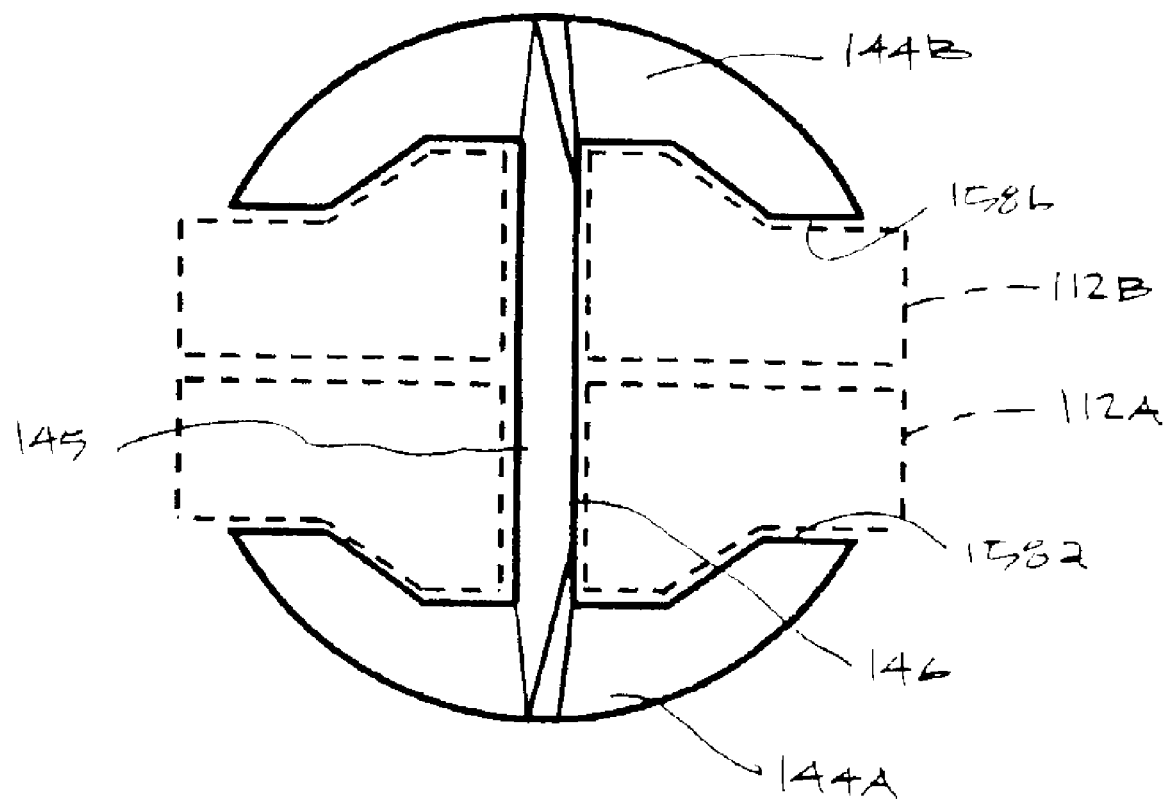
FIG. 5A is an end view of the reciprocatable member of FIG. 3 with first and second jaws in phantom view.
Figure 5B:
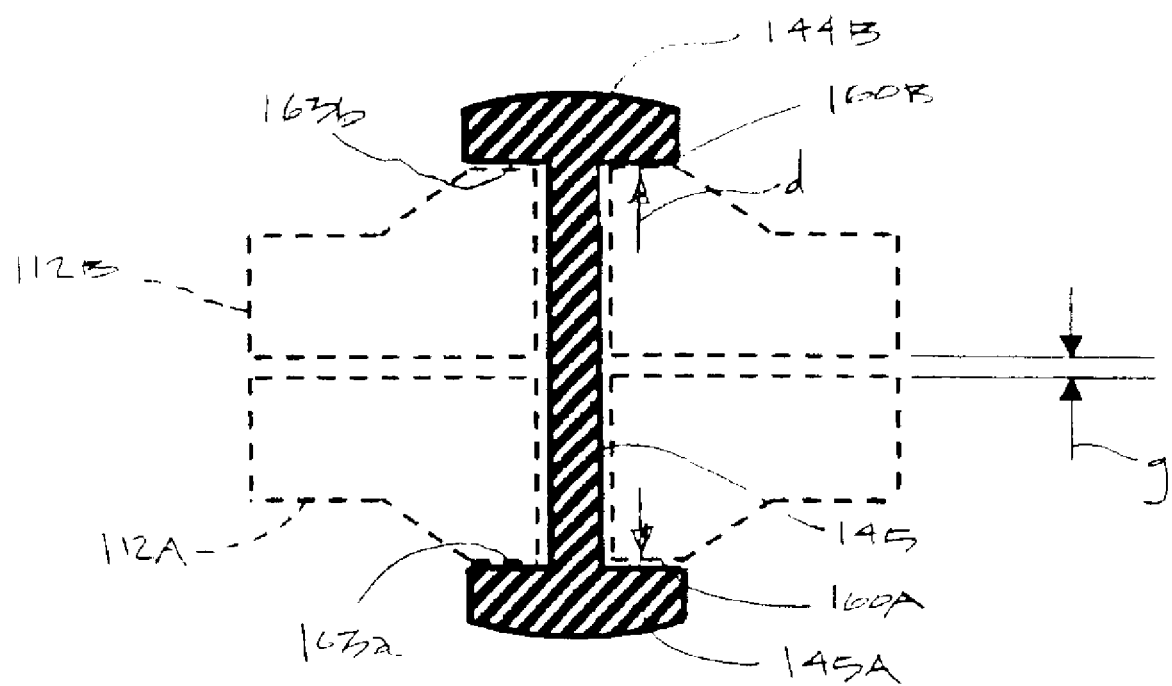
FIG. 5B is a sectional view of the reciprocatable member of FIG. 3 taken along line 5A—5A of FIG. 3.

The perspective and plan views (FIGS. 3 and 4) more particularly illustrate the cam surfaces of reciprocating member 140 de-mated from jaws 112A and 112B. FIG. 5A shows an end view of "I"-beam shape of the reciprocating member 140 with the jaws 112A and 112B in phantom view. From FIGS. 3, 4 and 7B, it can be easily understood how the jaw assembly 100 can apply very high compressive pressures to engaged tissue. The transverse element 145 of the reciprocating member 140 defines a transverse dimension d between the innermost surfaces 158a and 158b of the flanges of the reciprocating member and the cooperating medial and distal outer surfaces 160A and 160B of the jaws (see FIGS. 6, 7A and 7B). The selected transverse dimension d between the flanges or shoulders 144A and 144B thus further defines the engagement gap g between the engagement planes 150a and 150b of the jaws in the closed position. It has been found that very high compression of tissue combined with controlled Rf energy delivery is optimal for welding the engaged tissue volume contemporaneous with transection of the tissue. Preferably, the engagement gap g between the engagement planes ranges from about 0.001" to about 0.050" for most tissue volumes. More preferably, the gap g between the engagement planes ranges from about 0.001" to about 0.010". As can be seen in FIGS. 3, and 5B, the medial portion 141" of the reciprocating member 140 retains an "I"-beam shape with inner surface portions 163a and 163b that engage the cooperating medial outer surfaces of the jaws. Thus, the entire length L of the jaws can be maintained in a fixed spaced-apart relationship to define a consistent engagement gap g—no matter the length of the jaws.

It should be appreciated that jaw assembly 100 can be provided with mechanisms for adjusting the transverse dimension d between the inner surfaces of flanges 144A and 144B of the reciprocating member 140 as are disclosed in co-pending U.S. patent application Ser. No. 09/017,452 filed Dec. 13, 2001 titled Electrosurgical Jaws for Controlled Application of Clamping Pressure which is incorporated herein by reference. That application discloses mechanisms that allow the operator (i) to adjust the transverse dimension d between the cam surfaces of shoulders 144A and 144B between pre-selected dimensions, or (ii) to allow for dynamic adjustment of the transverse dimension d in response to the tissue volume captured between the paired jaws.

Figure 6:
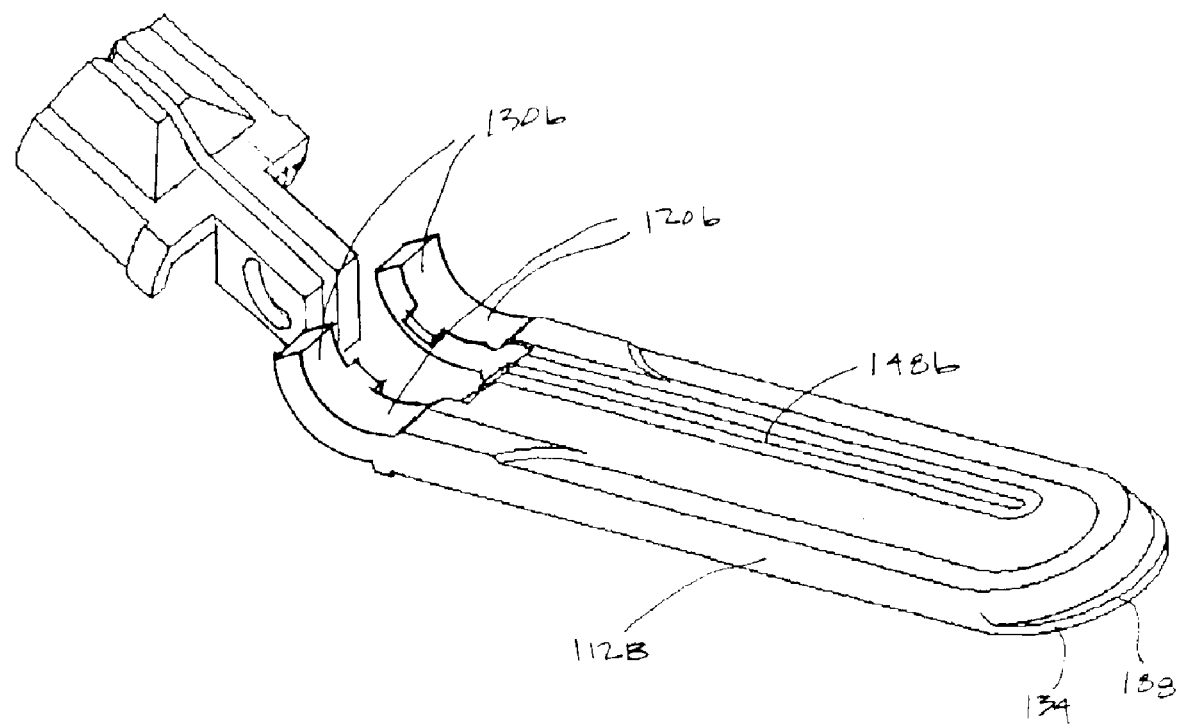
FIG. 6 is a perspective view of a de-mated jaw of the Type "A" electrosurgical working end of FIGS. 1–2.

FIG. 6 shows an exemplary jaw de-mated from the jaw assembly 100 that exposes the cam engagement surfaces 120b and 130b of the member. An additional unique feature of the invention is the fact that the cooperating jaws can be identical to one another, thus simplifying the manufacturing process. Since the jaw members can be identical, metal injection molds costs can be reduced.

Figure 7A:
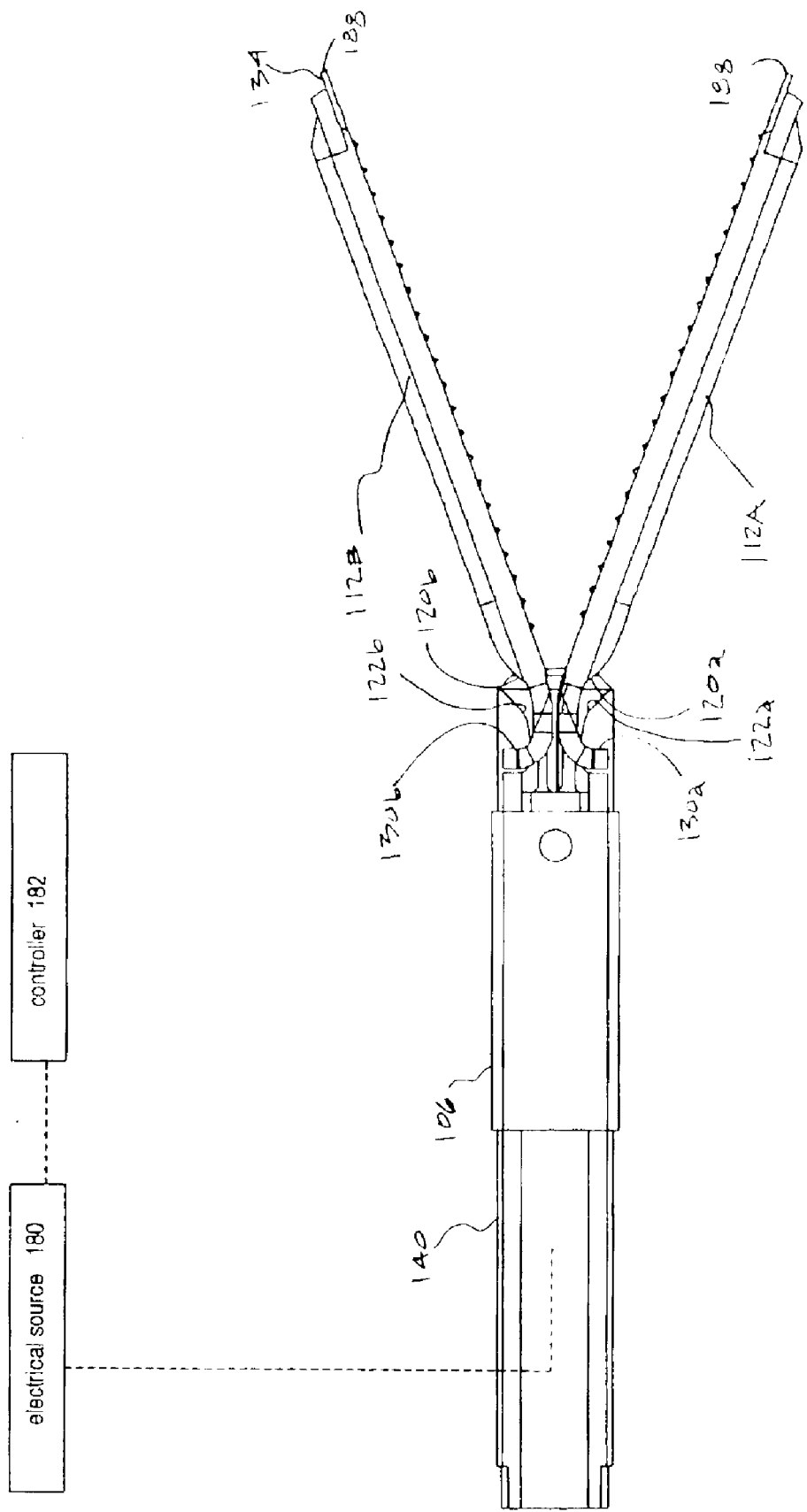
FIG. 7A is a side view of working end of FIGS. 1 and 2 with the reciprocatable member being retracted to apply opening forces on the paired jaws.
Figure 7B:
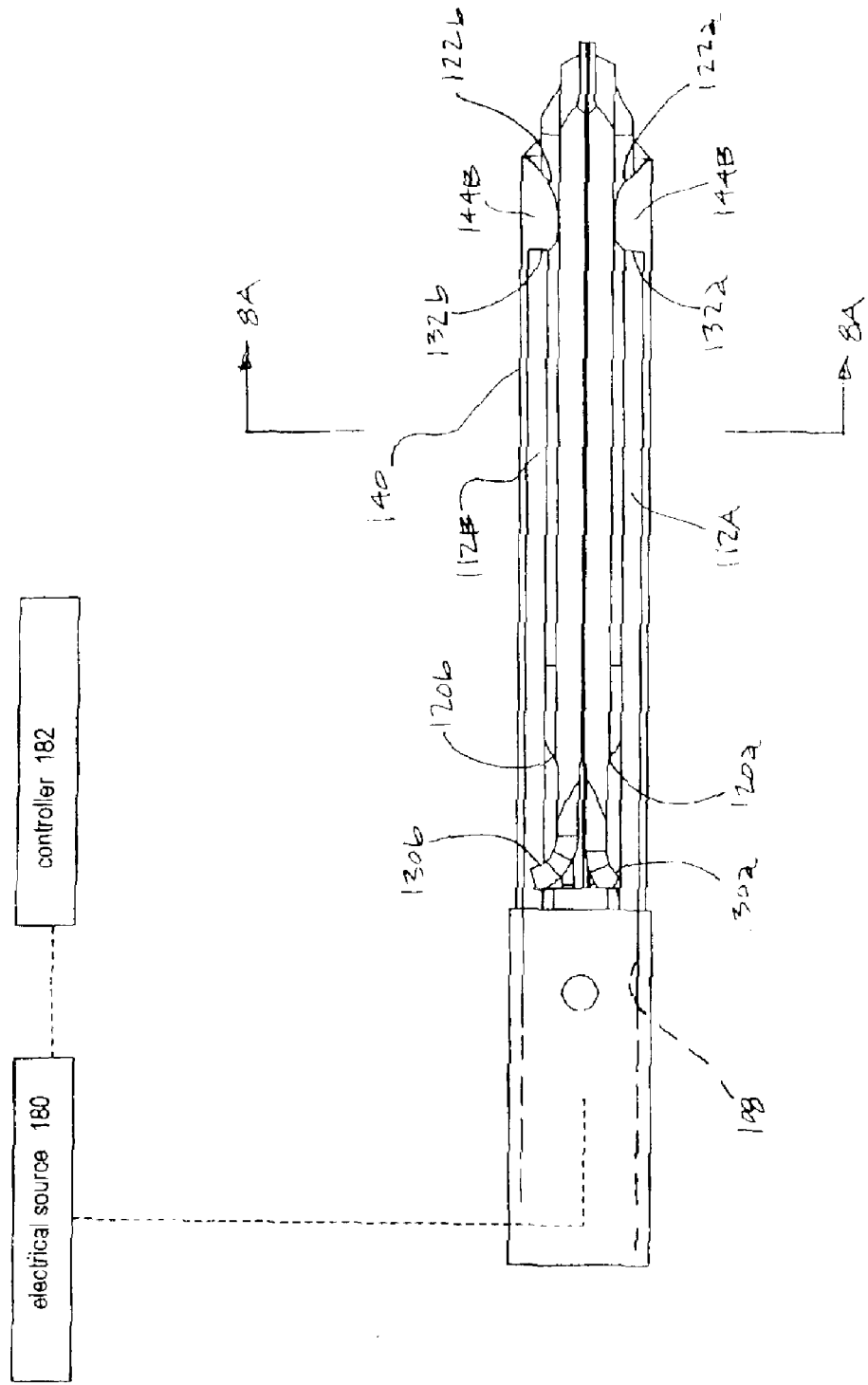
FIG. 7B is a side view similar to FIG. 7A showing the reciprocatable member fully extended to apply high compressive forces over the length of the paired jaws.

FIGS. 7A and 7B more particularly show the actuation of the reciprocating member 140 from a first retracted position to a second extended position to move the jaws 112A and 112A from the first open position to the second closed position. Referring to FIG. 7A, it can be seen that the translatable member 140 is being moved in the proximal direction so that the proximal-facing surfaces 132a and 132b of reciprocating member 140 abut the outer surfaces 130a and 130b of the jaws thus forcing the jaws apart, for example to apply dissecting forces to tissues. FIG. 7B shows the reciprocating member 140 after having been fully extended in the distal direction so that the distal-facing surfaces 122a and 122b of reciprocating member 140 have ridden up and over the proximal arcuate surfaces 120a and 120b of the jaws (and medial outer surfaces 160A' and 160B') thus forcing the jaws together.

Of particular interest, the jaws can rollably contact one another along the interface 170 between inner surfaces 172a–172b of the first end 118 of the jaws (see FIGS. 6, 7A and 7B). Thus, the jaw assembly does not need to define a true single pivot point as is typical of hinge-type jaws known in the art. The pivotable action of the jaws along interface 170 can best be described as a rolling pivot that optionally can allow for a degree of dynamic adjustment of the engagement gap g' at the proximal end of the jaws. The jaws elements can be retained relative to one another and the introducer sleeve 106 by means of protruding elements 175 (FIG. 6) that couple with arcuate slots 176 in an internal member 177 that is fixedly carried in bore 108 of introducer sleeve 106. Alternatively, outwardly protruding elements 178 can cooperate with slots in the wall of introducer sleeve 106 (not shown). As also shown in FIG. 6, the jaw assembly can (optionally) include springs for urging the jaws toward the open position. Electrical leads indicated at 109a–109b are shown in FIG. 6 for coupling a voltage source (radiofrequency generator) 180 and controller 182 to the electrode arrangement 155.

In one preferred embodiment shown in FIGS. 1 and 2, the first (lower) jaw 112A carries an exposed conductive material or electrode 155 together with an exposed variably resistive matrix 185 in the jaw's engagement plane 150a. The jaw assembly carries a return electrode in any of three locations, or any combination thereof: (i) in a portion of the opposing engagement surface 150b of upper jaw 112B, (ii) in the transverse element 145 of the reciprocating member 140; or (iii) in laterally outward portions of the lower jaw 112A that surround the variably resistive matrix 185.

Figure 8A:
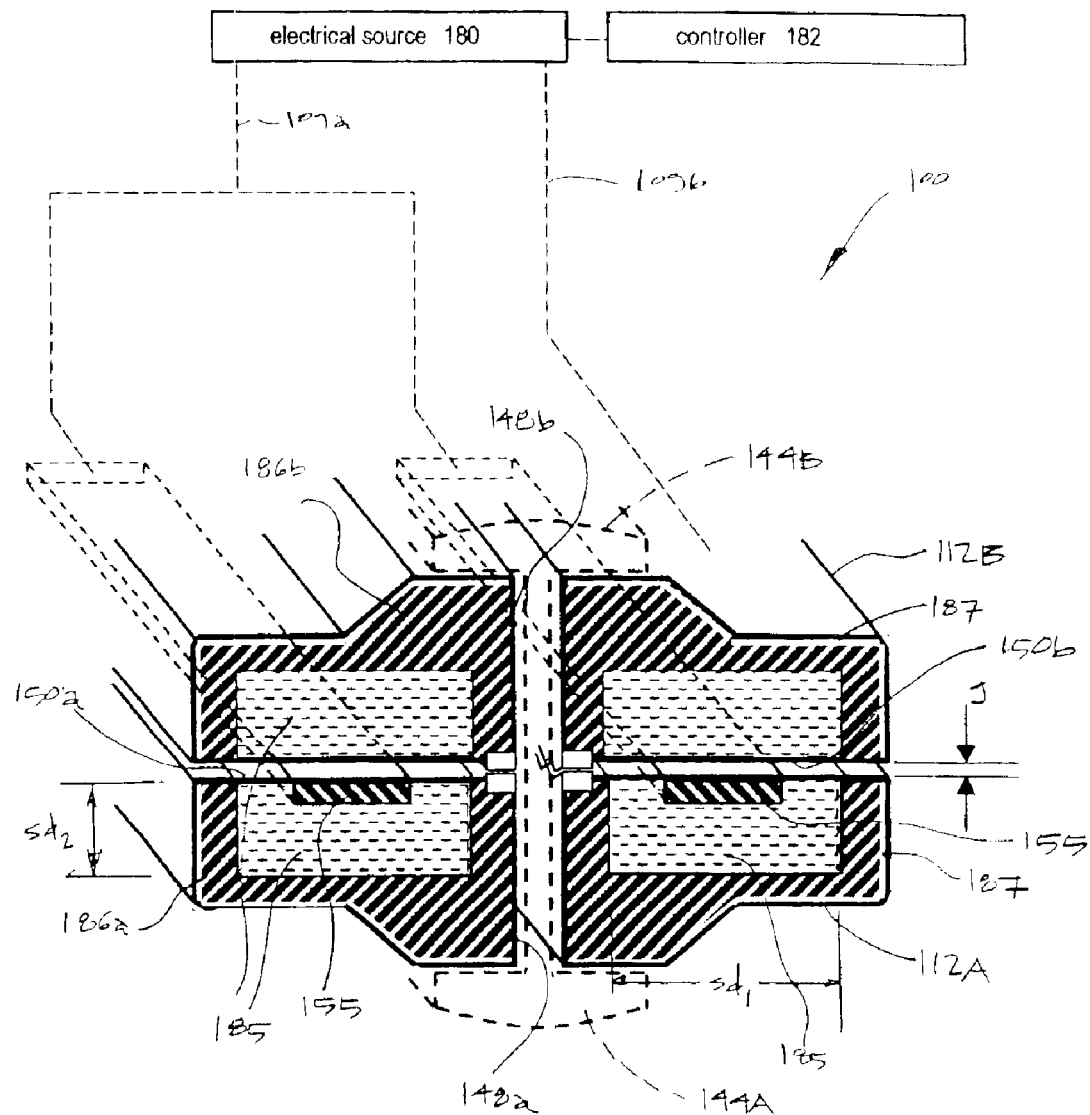
FIG. 8A is a sectional view of the Type "A" electrosurgical jaw taken along line 8A–8A of FIG. 7B illustrating the conductive component carried in one jaw and a variable resistive matrix carried in both jaws.

The sectional view of FIG. 8A more particularly illustrates the relevant conductive and variably resistive components within the body of the lower jaw 112A for controllably delivering energy to tissue for sealing or welding purposes. The engagement surface 150a of jaw 112A has the exposed conductive material (electrode) indicated at 155 that is both electrically conductive and thermally conductive. For example, the conductive material 155 can comprise a machined metal, a formed metal or a molded metal having a substantial thickness—that can be conductively bonded to the positive temperature coefficient (PTC) variably resistive matrix 185 described next. Alternatively, the conductive material 155 can comprise a thin film deposit of any suitable material known in the art (e.g., gold, platinum, palladium, silver, stainless steel, etc.) having any suitable thickness dimension, for example, ranging from about of 0.0001" to 0.020". The width of the conductive material 155 can be any suitable dimension depending on the jaw dimension.

As can be seen in FIG. 8A, the jaw 112A has an engagement surface with an exposed conductive material 155 at least partially surrounded by PTC matrix 185 that is variably resistive in response to temperature changes therein is carried adjacent to, and inward of, the surface conductive material 155. The structural body portion 186a of jaw 112A can be any suitable metal or other material having sufficient strength to apply high compressive forces to the engaged tissue, and typically carries an insulative coating (at least on its outer portions). As shown in FIG. 8A, the body portion 186a of jaw 112A preferably (but optionally) has a thin insulated coating 187 about its surface to prevent electrical energy delivery to tissues about the exterior of the jaw assembly and between the body 186a and the PTC matrix 185.

The conductive portion (electrode) 155 exposed in the engagement plane 150a is coupled by an electrical lead 109a to a voltage (Rf) source 180 and controller 182. The matrix 185 can have any suitable cross-sectional dimensions, indicated generally at $sd_1$ and $sd_2$, and preferably such a cross-section comprises a significant fractional volume of the jaw body to provide a thermal mass for optimizing passive conduction of heat to tissue as will be described below.

It can be seen in FIG. 8A, a substantial portion of the surface area of engagement plane 150a comprises the PTC resistive matrix 185. Preferably, the matrix 185 comprises at least 10% of the surface area of engagement plane 150a of an electrosurgical jaw, wherein the engagement plane is defined as the tissue-contacting surface of the jaw. More preferably, the PTC matrix 185 comprises at least 25% of the surface area of engagement plane 150a of such a jaw. Still more preferably, the PTC matrix 185 comprises at least 50% of the surface area of the jaw's engagement plane 150a.

Of particular interest, still referring to FIG. 8A, the variably conductive matrix 185 comprises a polymeric material having a temperature-dependent resistance. Such materials are sometimes known as polymer-based "temperature coefficient" materials that exhibit very large changes in resistance with a small change in body temperature. This change of resistance with a change in temperature can result in a "positive" coefficient of resistance wherein the resistance increases with an increase in temperature (a PTC or positive temperature coefficient material). The scope of the invention also includes a variably conductive matrix 185 with a "negative" coefficient of resistance (and NTC material) wherein its resistance decreases with an increase in temperature.

In one preferred embodiment, the PTC matrix 185 is a ceramic layer that is engineered to exhibit unique resistance vs. temperature characteristics that is represented by a positively slope temperature-resistance curve in FIG. 8A. More in particular, the matrix 185 maintains a low base resistance over a selected temperature range with a dramatically increasing resistance above a selected narrow temperature range of the material (sometimes referred to herein as switching range; see FIG. 8B). For example, the base resistance can be low, or electrical conductivity can be high, between about 37° C. and 65° C., with the resistance increasing greatly between about 55° C. and 80° C. In another embodiment, the PTC matrix 185 is characterized by a more continuously positively sloped temperature-resistance as shown curve in FIG. 8C over the range of 37° C. to about 80° C.

Figure 8B:
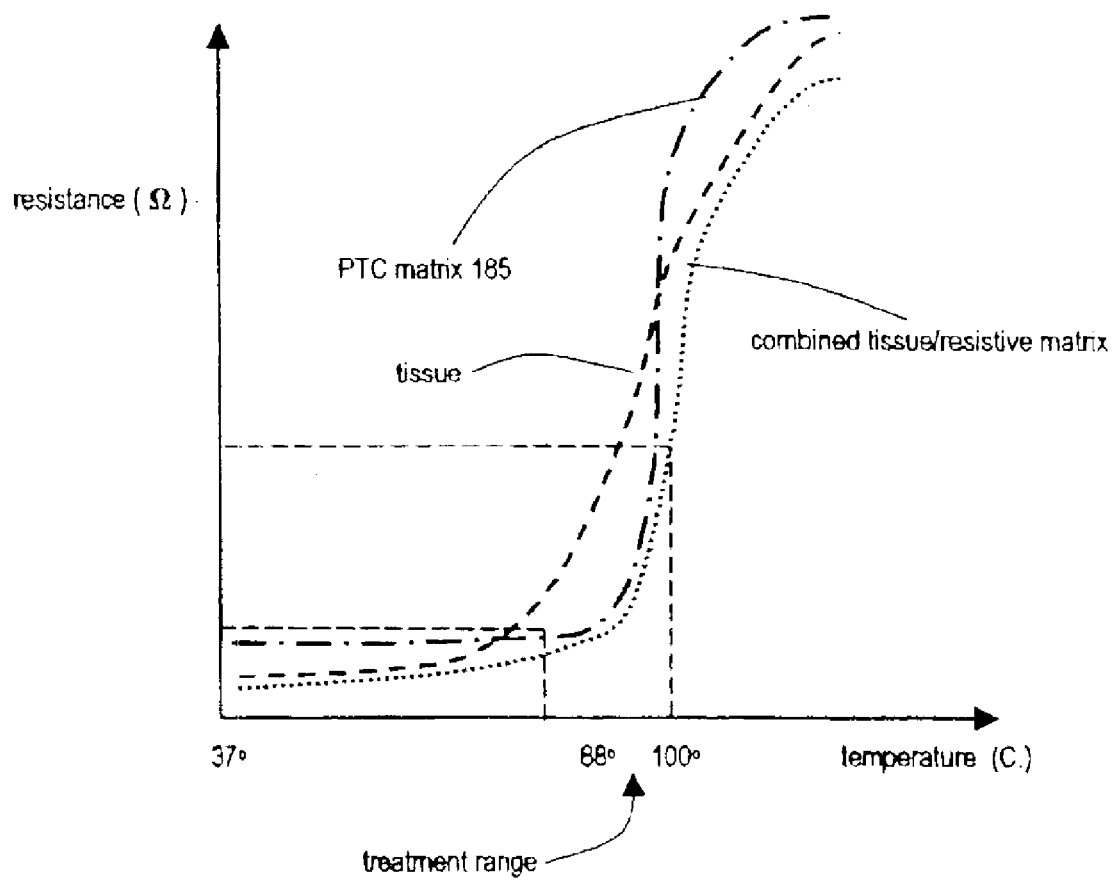
FIG. 8B is a graph showing the temperature-resistance profile of a variable resistive matrix carried in the jaw of FIG. 8A, the impedance of tissue and the combined resistance of the variable resistive matrix and tissue as measured by a system controller.

One aspect of the invention relates to the use of a PTC matrix 185 as described in FIG. 8B in a jaw's engagement plane with a selected switching range between a first temperature ($T_1$) and a second temperature ($T_2$) that approximates the targeted tissue temperature for a contemplated tissue sealing or welding objective. The selected switching range, for example, can be any substantially narrow 1°–10° C. range that is determined to be optimal for tissue sealing or welding (e.g., any 5° C. range between about 50°–200° C.) or for another thermotherpy. A more preferred switching range can fall within the larger range of about 50°–90° C.

No matter the character of the slope of the temperature-resistance curve of the PTC matrix 185 (see FIGS. 8B and 8C), a preferred embodiment has a matrix 185 that is engineered to have a selected resistance to current flow across its selected dimensions in the jaw assembly when at 37° C. ranging from about 0.0001 ohms to 1000 ohms. More preferably, the matrix 185 has a designed resistance across its selected dimensions in the jaw when at 37° C. ranging from about 1.0 ohm to 1000 ohms. Still more preferably, the matrix 185 has with a designed resistance across its selected dimensions when at 37° C. ranging from about 25 ohms to 150 ohms. In any event, the selected resistance across the matrix 185 in an exemplary jaw at 37° C. exceeds the resistance of the tissue or body structure targeted for treatment. The matrix 185 further is engineered to have a selected resistance that substantially prevents current flow therethrough corresponding to a selected temperature that constitutes the high end (maximum) of the targeted thermal treatment range. Such a maximum temperature for tissue welding can be a selected temperature between about 50° C. and 100° C. More preferably, the selected temperature at which the matrix's selected resistance substantially prevents current flow occurs at between about 60° C. and 90° C.

In a first mode of operation, it can be understood that the initial delivery of Rf energy to conductor or electrode 155 will thereby apply Rf energy to (or cause active ohmic heating of) tissue engaged between jaws 112A and 112B. Further, the delivery of Rf energy to electrode 155 will be conducted, in part, through the PTC matrix 185 in a path to a return electrode—no matter the location of the return electrode (or and combination thereof) as described above. The engaged tissue is thus elevated in temperature by ohmic or "active" Rf heating. The paired jaws' components, including the PTC matrix 185, will increase in temperature as caused by conduction of heat from the transient high temperatures of tissue—which were heated by caused by Rf densities therein (ohmic heating).

At a selected temperature at the maximum of the targeted treatment range, the PTC matrix 185 will no longer contribute to ohmic tissue heating due to termination of current flow therethrough. However, the mass of the PTC matrix 185 will still conduct heat to engaged tissue. As the PTC matrix 185 falls below the targeted treatment range, the matrix 185 again will contribute to ohmic tissue heating via current paths therethrough from electrode 155. By this means of energy delivery, the mass of the jaw body will be modulated in temperature, similar to the engaged tissue, at or about the targeted treatment range. Of particular interest, the jaw body will apply energy to engaged tissue by ohmic heating, or by conduction (or radiation) of thermal effects in a self-modulating manner.

A suitable PTC material can be fabricated from high purity semi-conducting ceramics, for example, based on titanate chemical compositions (e.g., $BaTiO_3$, $SrTiO_3$, etc.). The specific resistance-temperature characteristics of the material can be designed by the addition of dopants and/or unique materials processing, such as high pressure forming techniques and precision sintering. Suitable PTC materials are manufactured by several sources and can be obtained, for example, from Western Electronic Components Corp., 1250-A Avenida Acaso, Camarillo, Calif. 93012. Another manner of fabricating the PTC resistive matrix 185 is to use a commercially available epoxy that is doped with a type of carbon. In fabricating a PTC matrix 185 in this manner, it is preferable to use a carbon type that has single molecular bonds. It is less preferable to use a carbon type with double bonds which has the potential of breaking down when used in thin layers, thus creating the potential of an electrical short circuit between the conductor (electrode) 155 and a return electrode carried within the jaw assembly.

As can be seen in FIG. 8A, the conductive material or electrode 155 is operatively connected to the voltage (Rf) source 180 by electrical lead 109a that defines a first polarity. As described previously, return electrode functionality can be carried in any of three components of the jaw assembly, or any combination thereof: (i) in a portion of the opposing engagement surface 150b of upper jaw 112B, (ii) in the transverse element 145 of the reciprocating member 140; or (iii) in laterally outward portions of the lower jaw 112A outwardly adjacent to the PTC matrix 185. In the embodiment of FIG. 8A, the body portions 186a and 186b of the lower and upper jaws 112A and 112B have an opposing polarity as defined by coupling to electrical source by lead 109b. Further, the slidable contact of the jaw body portions 186a and 186b with transverse element 145 of reciprocating member 140 makes it function with the opposing polarity. In the preferred embodiment depicted in FIG. 8A, the upper jaw 112B also carries a PTC matrix 185 that covers a substantial portion of the engagement surface 150b. The material of the PTC matrix can be identical in both the lower and upper jaws.

The manner of utilizing the jaw assembly 100 of FIG. 8A to perform a method of the invention can be understood as engaging and compressing tissue between the first and second engagement surfaces 150a and 150b of jaws 112A and 112B and thereafter delivering Rf energy from conductor 155 and PTC matrix 185 to maintain a selected temperature in the engaged tissue for a selected time interval. For example, the jaw assembly is provided with a PTC matrix 185 that has a targeted treatment range in a region below about 90° C. With the jaws in the closed position and the engagement planes 150a and 150b engaging tissue, the operator actuates a switch that delivers Rf energy from the voltage (Rf) source 180 to the conductor 155. At normal tissue temperature, the low base resistance of the PTC matrix 185 allows unimpeded Rf current flow from the voltage source 180 through engagement surface 150a and tissue to the return electrode components as described above via lead 109b. It can be understood that the engaged tissue initially will have a substantially uniform impedance to electrical current flow, which will increase substantially in proximity to engagement surfaces 150a and 150b as the engaged tissue loses moisture due to ohmic heating.

Following an arbitrary time interval, the impedance of tissue proximate to engagement surfaces 150a and 150b will be elevated, and the higher tissue temperature will instantly conduct heat to the PTC matrix 185 in each jaw. In turn, the PTC matrix 185 will reach its limit and terminate Rf current flow therethrough. Such automatic reduction of active Rf energy application can thus prevent any substantial dehydration of tissue proximate to PTC matrix 185. By thus maintaining the desired level of moisture in tissue proximate to the engagement planes, the jaw assembly can more effectively apply energy to the tissue. Such energy application can extend through thick engaged tissue volumes while causing very limited collateral thermal effects. Thereafter, as the temperature of the engaged tissues falls by thermal relaxation and the lesser Rf energy density, the temperature of the matrix 185 will fall below the threshold of the targeted treatment range. This effect, in turn, will cause increased Rf current flow through the assembly and matrix to the engaged tissues to again increase the tissue temperature by increased ohmic heating. By the above-described mechanisms of causing the PTC matrix 185 to be maintained in the treatment range, the actual Rf energy applied to the engaged tissue can be precisely modulated to maintain the desired temperature in the tissue. Further, the composition that comprises matrix 185 can comprise a substantial volume of the jaws' bodies and the thermal mass of the jaws, when elevated in temperature, can deliver energy to the engaged tissue by means of passive conductive heating—at the same time Rf energy delivery causes lesser active (ohmic) tissue heating. This balance of active Rf heating and passive conductive (or radiative) heating can maintain the targeted temperature for any selected time interval.

In summary, one method of the invention comprises the delivery of Rf energy from a voltage source 180 to tissue via a conductor in a jaw assembly at least partly through a PTC material 185 wherein the thermally-sensitive resistor material has a selected temperature-resistance profile to provides low resistance at low tissue temperatures and a very high resistance above the targeted temperature range for tissue sealing or welding. In operation, the working end automatically modulates active Rf energy density in the tissue as the temperature of the engaged tissue conducts heat back to the PTC material 185 to cause move the matrix along its selected temperature-resistance curve. In the treatment range, the Rf current flow thus can be modulated without the need for thermocouples or any other form of feedback circuitry mechanisms to modulate Rf power from the source. Most important, it is believed that this method of the invention will allow for immediate modulation of actual Rf energy application along the entire length of the jaws, which is to be contrasted with prior art instruments that utilize a temperature sensor and feedback circuitry. Such sensors or thermocouples measure temperature only at a single location in the jaws, which typically will not be optimal for energy delivery over the length of the jaws. Such temperature sensors also suffer from a time lag. Further, such temperature sensors provide only an indirect reading of actual tissue temperature—since a typical sensor can only measure the temperature of the electrode.

In another mode of operation, the system controller 182 coupled to source 180 can acquire data from the current flow circuitry that is coupled to first and second polarity electrodes in the jaw (in any locations described previously) to measure the blended impedance of current flow between the first and second polarity conductors through the combination of (i) the engaged tissue and (ii) the PTC matrix. Another method of the invention thus can include provide algorithms within the system controller 182 to modulate, or terminate, power delivery to working end based on the level of the blended impedance as defined above. The method can further include controlling energy delivery by means of power-on and power-off intervals, with each such interval having a selected duration ranging from about 1 microsecond to one second. The working end and system controller 182 can further be provided with circuitry and working end components of the type disclosed in Provisional U.S. Patent Application Ser. No. 60/339,501 filed Nov. 9, 2001 titled Electrosurgical Instrument which is incorporated herein by reference.

Figure 8C:
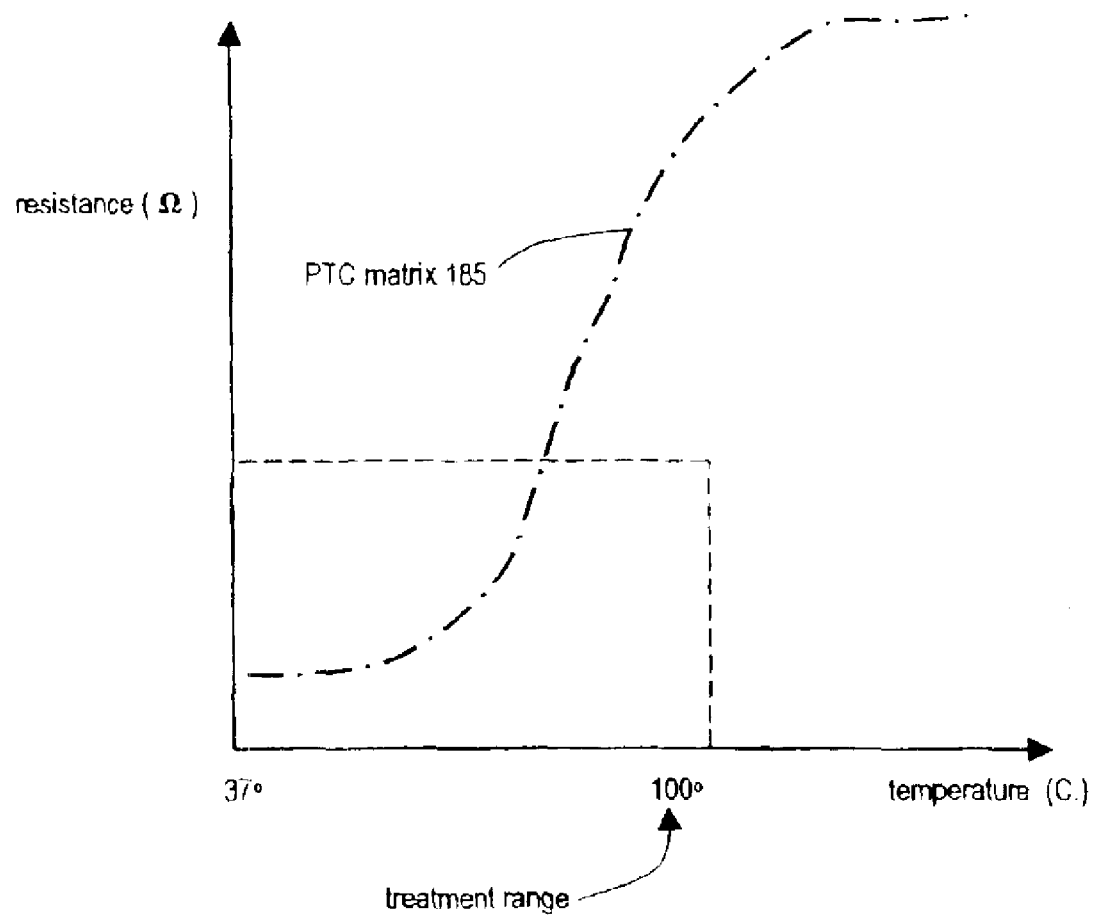
FIG. 8C is a graph showing an alternative temperature-resistance profile of a variable resistive matrix carried in the jaw of FIG. 8A.

In another mode of operation, the system controller 182 can be provided with algorithms to derive the temperature of the resistive PTC matrix 185 from measure impedance levels—which is possible since the matrix is engineered to have a selected resistance at each selected temperature over the temperature-resistance curve (see FIGS. 8B–8C. Such temperature measurements can be utilized by the system controller 182 to modulate, or terminate, power delivery to engagement surfaces based on the temperature of the PTC matrix 185. This method also can control energy delivery by means of the power-on and power-off intervals as described above.

Referring back to FIG. 2, the distal (second) end 133 of the jaws carries a thin lip 134 extending outwardly from the jaw body. It has been found useful to provide an electrode in lip 134 for surface coagulation of tissues. In one preferred embodiment, an independent electrode 188 is carried in lip 134 that can be any thin film conductive material carried at the surface of jaws and coupled to an electrical source (not shown), for example cooperating with a ground pad. In another embodiment, the electrode 188 can comprise an exposed portion of the conductive lower jaw body 186*a* and upper jaw body 186*b* wherein the insulative layer 187 removed from the lips 134 (cf. FIG. 8A).

Figure 8D:
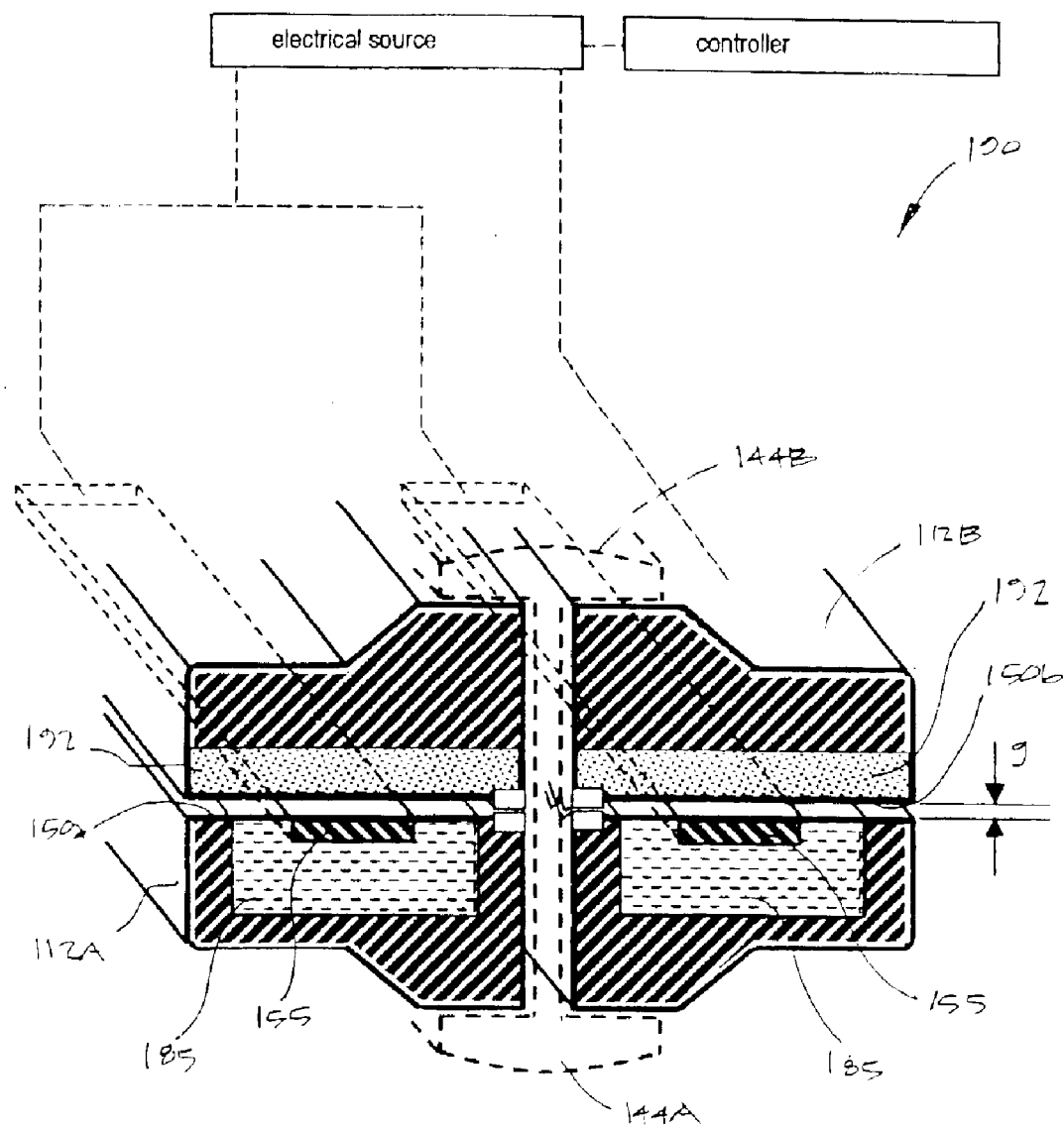
FIG. 8D is a sectional view of an alternative Type "A" electrosurgical jaw illustrating the conductive component and temperature-sensitive resistive matrix of the jaw assembly carried in a one jaw with the other jaw having a insulative engagement surface.

FIG. 8D shows an alternative embodiment of jaw assembly 190 that carries all the same components as described previously in the embodiment of FIG. 8A. The difference is that the engagement plane 150*b* of upper jaw 112B carries a fully insulated layer indicated at 192. It has been found that such a configuration can function well in very small instruments adapted for engaging small tissue volumes.

Figure 8E:
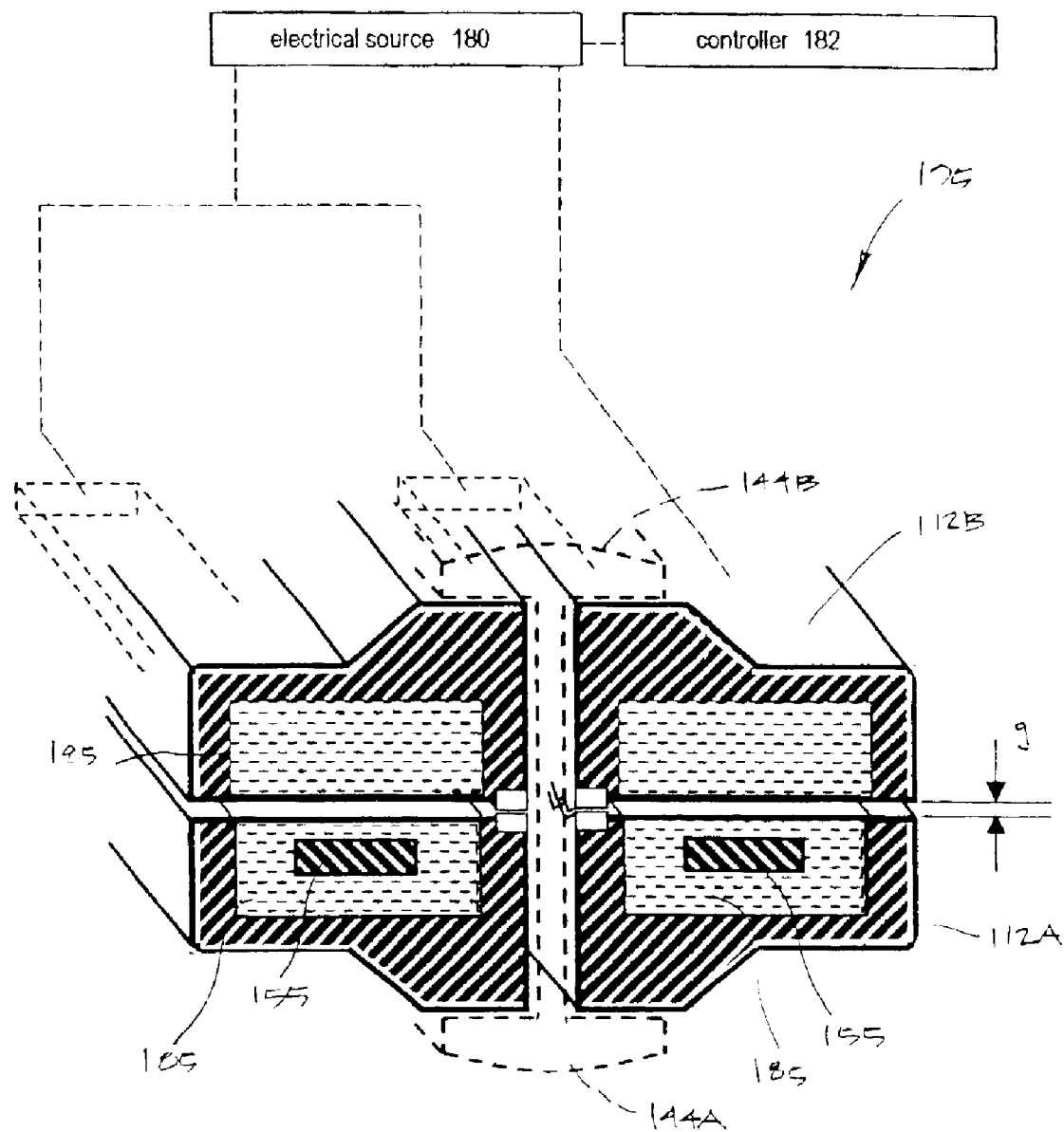
FIG. 8E is a sectional view of another alternative Type "A" electrosurgical jaw illustrating the conductive component embedded in the temperature-sensitive resistive matrix in one jaw.

FIG. 8E illustrates another alternative embodiment of jaw assembly 195 that carries components that are similar to those described in the embodiments of FIGS. 8A and 8D. However, in this embodiment, the conductor 155 of the lower jaw 112A is carried in an interior portion of the PTC matrix 185. Thus, the conductor 155 has no exposed surface in engagement plane 150*a* of the lower jaw 112A. It has been found that such a configuration is useful in treating some very thin tissues since ohmic heating of tissue can be terminated altogether when the PTC matrix 185 reaches its selected switching range. In operation, the jaws can automatically modulate the application of energy to tissue between active Rf heating and passive conductive heating of the targeted tissue at a targeted temperature level.

2. Type "B" jaw assembly. FIGS. 9–10 illustrate an exemplary Type "B" jaw assembly 200 adapted for electrosurgery that again can weld and transect an engaged tissue volume. The jaw assembly 200 is carried at the distal end 204 of an introducer member 206 that has a bore 208 extending therethrough. The Type "B" embodiment is similar to the Type "A" embodiment except that the first (lower) jaw 212A is a fixed extension portion of rigid introducer member 206. As can be seen in FIGS. 9 and 10, the second (upper) jaw 212B is adapted to close or approximate about axis 215.

The opening-closing mechanism of jaw assembly 200 corresponding to the invention again provides cam surfaces for positive engagement between reciprocatable member 240 and the jaws (i) for moving the jaws to a (second) closed position to engage tissue under high compressive forces, and (ii) for moving the jaws toward the (first) open position thereby providing high opening forces to dissect tissue with outer surfaces of the jaw tips. The reciprocating member 240 operates as described previously to reciprocate within bore 208 of the introducer member 206. As can be seen in FIG. 10, the distal end portion 242 of reciprocating member 240 carries distal first and second laterally-extending flange portions 244A and 244B with the blade-carrying transverse element 245 extending therebetween. The blade-carrying member slides within channels 248*a* and 248*b* in the jaws.

In the exemplary embodiment of FIGS. 9 and 10, the first and second jaws 112A and 112B again define engagement surfaces or planes 250a and 250b that deliver energy to engaged tissue. The engagement planes carry a conductor 255 and a PTC matrix 285 in at least one of the jaws' engagement surfaces 250a and 250b. In the embodiment of FIGS. 9 and 10, the upper jaw 212B has a first end region 258 that, in the open position, defines a first (proximally-facing) arcuate cam surface indicated at 260 that is engaged by a first surface portion 262 of the reciprocatable member 240. The reciprocatable member 240 can be substantially identical to that of FIGS. 3 and 4. The first (proximal) end region 258 of the upper jaw, in the open position, further defines second (distally-facing) surface portions indicated at 270a and 270a' that are engaged by second surface 272 of reciprocatable member 240 for moving the jaw assembly to an open position.

Figure 11:
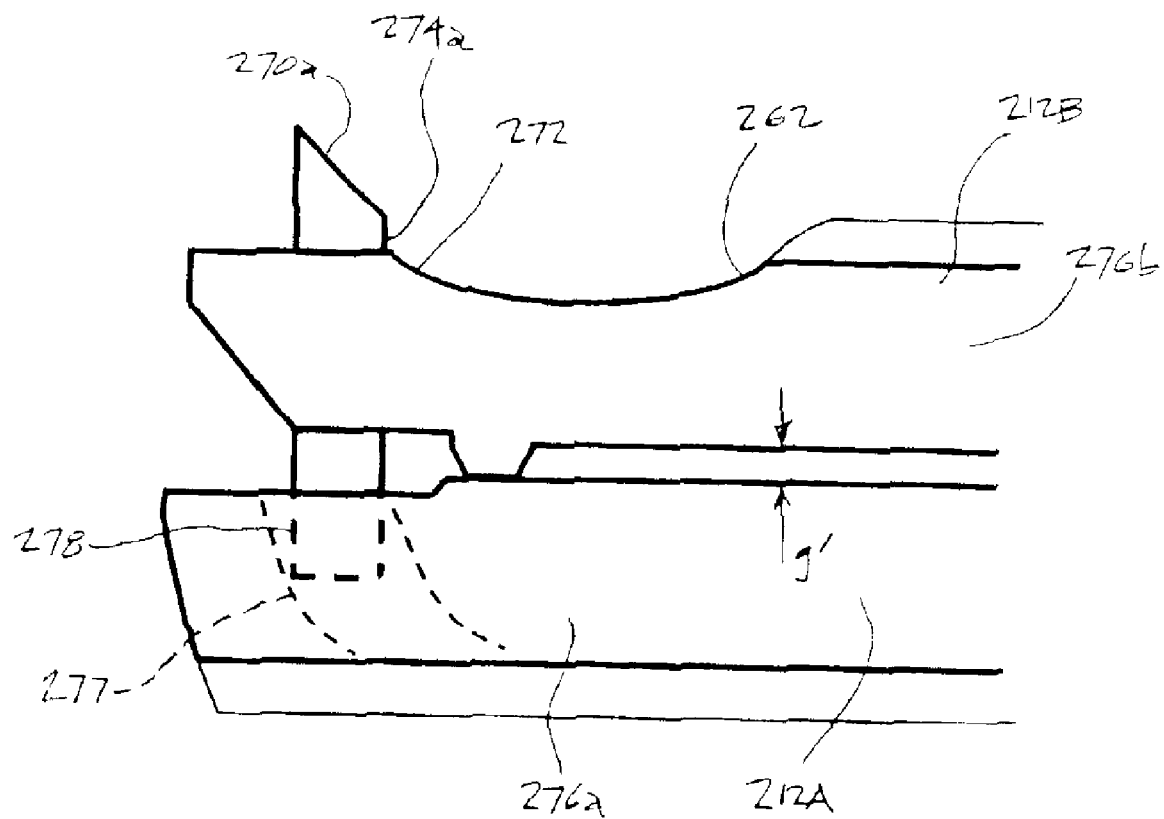
FIG. 11 is an enlarged view of a proximal (first) end portion of the Type "B" jaw of FIGS. 9–10 showing a projecting pin of the upper jaw that rotatably cooperates with an arcuate bore in the lower jaw to provide a jaw pivot with a selected degree of freedom of movement.

As can be seen best in FIG. 10, the cam surfaces 270a and 270a' are formed into pins or projecting elements 274 and 274' that serve multiple purposes. Referring to FIG. 11, the pins 274 and 274' extend through the upper jaw body 276b and are received within arcuate bores 277 in body 276a of lower jaw 212A. The lower portions 278 (collectively) of the pins 274 and 274' thus can retain upper jaw 212A and prevent it from moving axially or laterally relative to the jaw axis 215 while still allowing the jaw's rotation for opening and closing. The pin mechanism further allows for greatly simplified assembly of the instrument.

Of particular interest, the pins 274 and 274' provide additional functionality by providing a degree of "vertical" freedom of movement within the first (proximal) end portion 258 of the jaw. As can be seen in FIGS. 10 and 11, the distal laterally-extending flange portions 244A and 244B define a transverse dimension d (cf. FIG. 3) that in turn determines the dimension of the engagement gap g of the distal end of the jaws in the jaw-closed position (FIG. 10). The transverse dimension d equals the dimension between inner surfaces of flange portions 244A and 244B that slidably contact the outer surfaces of both jaws.

FIG. 10 further illustrates that reciprocatable member 240 carries separate proximal laterally-extending flange portions 294A and 294B with an optional different transverse dimension d' between inner surfaces thereof. A larger dimension d' between flange portions 294A and 294B that slidably contacts the proximal surfaces of both jaws can thus provide a different engagement gap g' at the proximal end of the jaws. This selected gap dimension g' can be larger than the engagement gap g at the distal end of the jaws—an effect that would not be possible with a hinged jaw that allows no "vertical" freedom of movement between the proximal ends of the jaws. It has been found that such a floating pivot is useful for engaging thick tissues. Further, the inner surfaces of the flanges 244A–244B and 294A–294B can carry a very slightly compressible material such as a Teflon (not shown) wherein slight compression of such material would allow the jaws' engagement surfaces to move slightly apart when engaging thick tissues.

3. Type "C" jaw assembly. FIGS. 12A–12D illustrate an exemplary Type "C" jaw assembly 300 that provides both electrosurgical functionality and improved grasping and dissecting functionality for endoscopic surgeries. In FIGS. 12A–12D, both the upper and lower jaws are shown in cut-away views to show internal cam surfaces of the upper jaw 312A and the reciprocatable member 240. The jaw assembly 300 carries engagement surfaces for applying electrosurgical energy to tissue as in the previously described embodiments, as well as cutting means for transecting the engaged tissue volume. The improvement of the Type "C" jaw assembly 300 relates to the ability of the jaw structure, in one mode of operation, to be used for general grasping and dissecting purposes wherein the distalmost tips 313 of the jaws can close tightly on tissue with little movement of the actuator lever in the handle of the instrument. At the same time, in another mode of operation, the jaw assembly 300 can close to apply very high compressive forces on the tissue to enable welding. Thus, the jaw structure provides (i) a first non-parallel jaw-closed position for grasping tissue with the distal jaws tips (FIG. 12C), and (ii) a second parallel jaw-closed position for high compression of tissue for the application of electrosurgical energy (FIG. 12D).

Figure 12A:
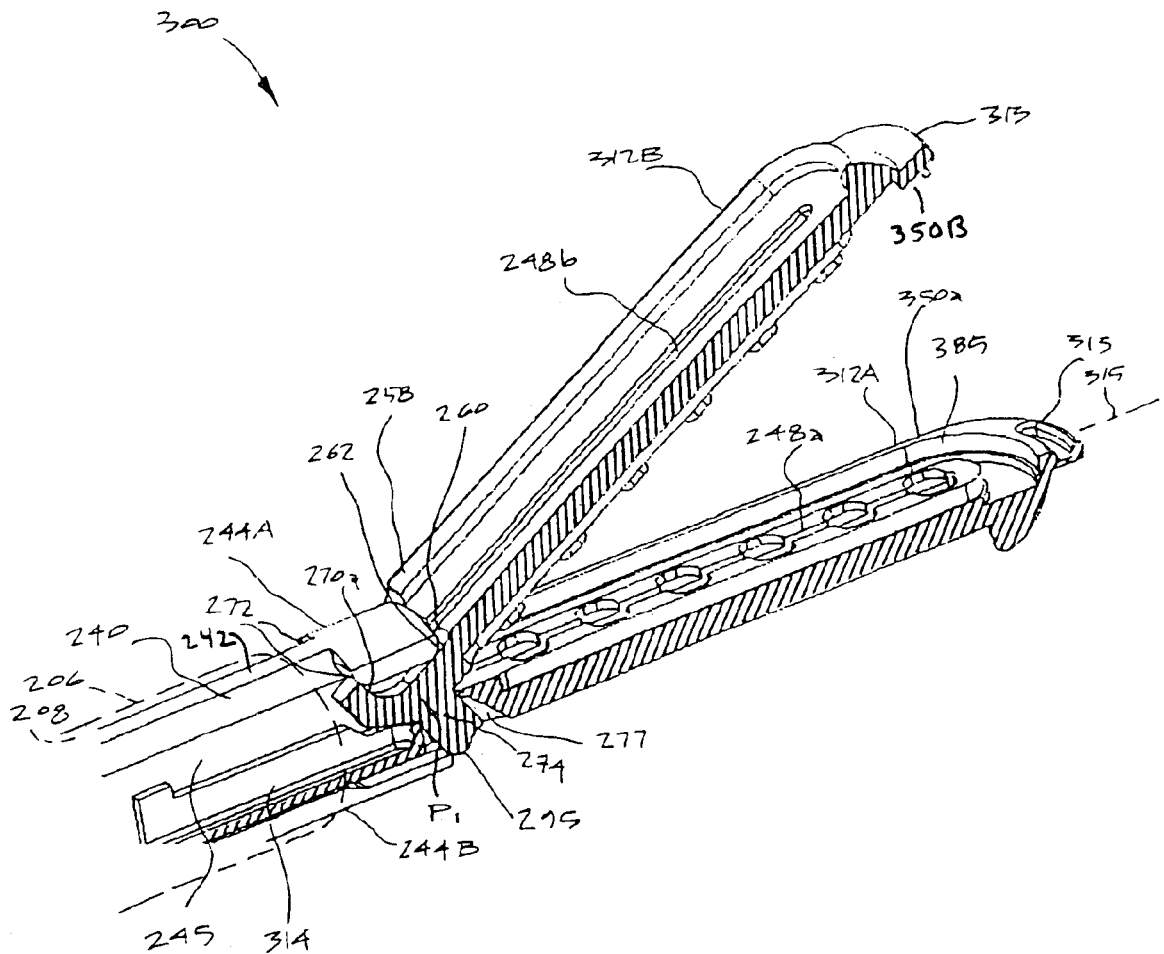
FIG. 12A shows a Type "C" jaw structure in an open position with the slidable extension member and jaws in a partially cut-away view to illustrate the jaw opening-closing mechanism.

Referring to FIG. 12A, the Type "C" embodiment again has an introducer member 206 that is similar to the Type "B" embodiment with first (lower) jaw 312A comprising a fixed extending portion 314 of the rigid introducer. As can be seen in FIG. 12A, the second (upper) jaw 312B is adapted to close or approximate about axis 315. The opening-closing mechanism of jaw assembly 300 provides cam elements and cooperating jaw surfaces for positive engagement between the reciprocatable member 240 as described previously (i) for moving the jaws to a closed position to engage tissue, and (ii) for moving the jaws toward the open position thereby providing high opening forces to dissect tissue with outer surfaces of the jaw tips 313.

The reciprocating member 240 (FIG. 13) operates as described previously to reciprocate within bore 208 of the introducer member 206 (FIG. 12A). As can be seen in FIG. 12A, the distal end 242 of the reciprocating member 240 again carries distal flange portions 244A and 244B with a blade-carrying transverse portion 245 therebetween. The transverse portion 245 slides within channels 248a and 248b in the paired jaws. In the exemplary embodiment of FIG. 12A, the first and second jaws 312A and 312B again define engagement surfaces 350a and 350b that can deliver electrosurgical energy to engaged tissue. The engagement planes preferably carry a conductive-resistive matrix 385 (not shown) in at least one of the jaws' engagement surfaces.

In the embodiment of FIG. 12A, the upper jaw 312B has a proximal end 258 that defines a first (proximally-facing) arcuate jaw surface 260 that is engaged by a first cam surface element 262 of reciprocatable member 240 for opening the jaw. The proximal end 258 of the upper jaw further defines second (distally-facing) jaw surface portions indicated at 270a and 270a' that are engaged by second cam element 272 of reciprocatable member 240 for moving the jaw assembly to an open position.

The embodiment of FIG. 12A shows that the upper jaw 312B has a floating primary pivot location indicated at $P_1$ that is provided by the projecting elements or rectangular pins 274 (collectively) on either side of the channel portions 248a that slidably extend into bores 277 (collectively) in the lower jaw body (cf. FIG. 11). The lower portions of the pins 274 thus allow upper jaw 312B to rotate while at the same time the pin-and-bore mechanism allows the upper jaw to move upwardly away from the lower jaw.

Of particular interest, the degree of "vertical" freedom of movement of the upper jaw allows for the system to "tilt" the distal tip 313 of upper jaw 312B toward the axis 315 to thereby allow the distal jaw tips 313 to grasp tissue. This is termed a non-parallel closed position herein. The tilting of the jaw is accomplished by providing a plurality of cam surfaces in the upper jaw 312B and the reciprocatable member 240.

Figure 12B:
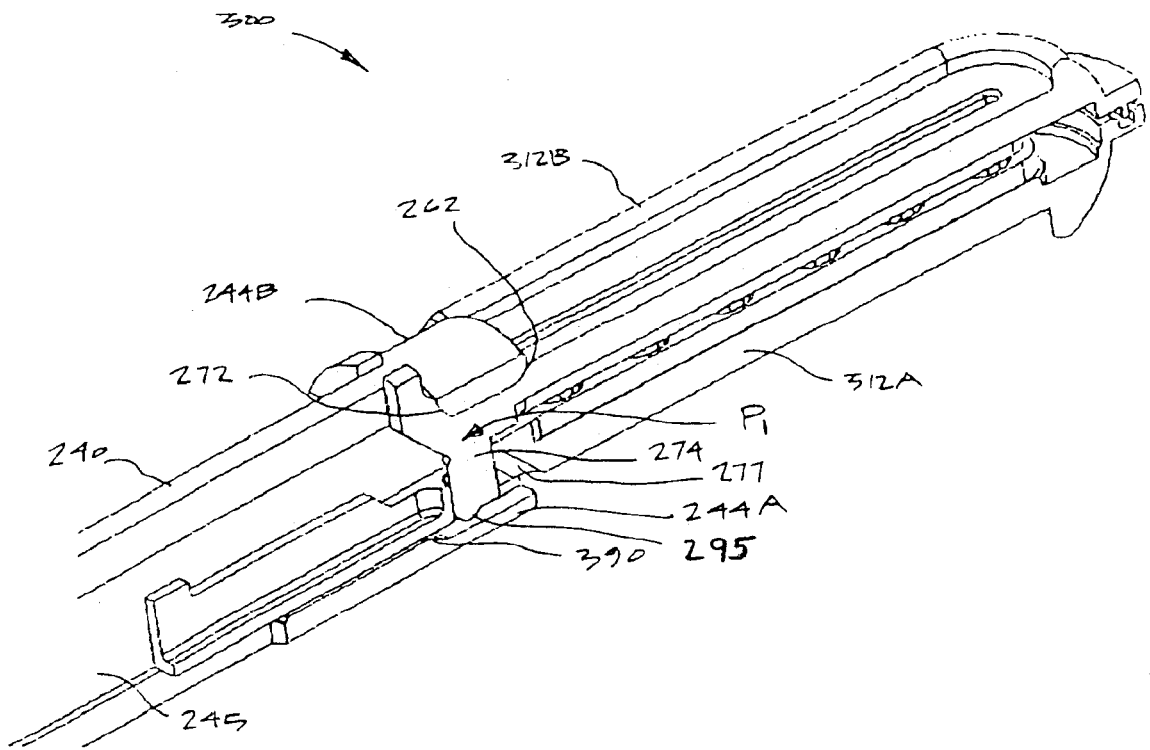
FIG. 12B shows the Type "C" jaw structure of FIG. 12A in a first closed position with the slidable extension member moving the jaws to a parallel condition.
Figure 12C:
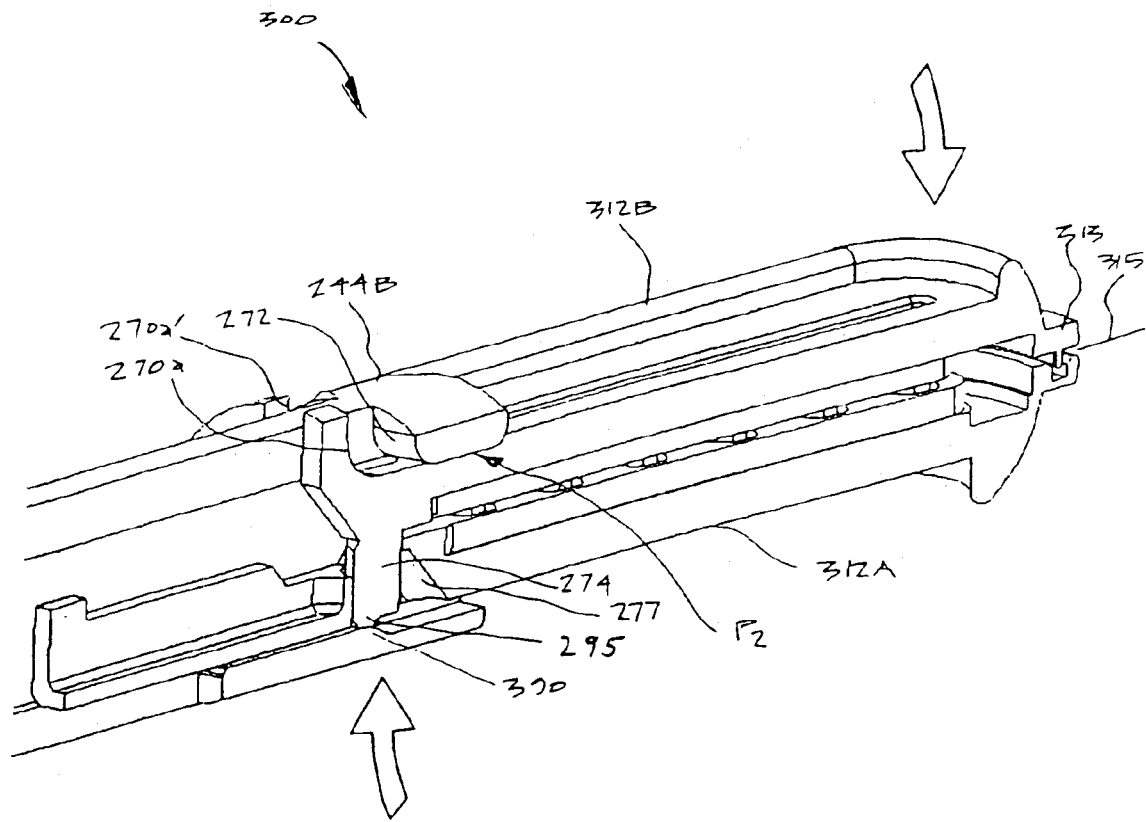
FIG. 12C shows the jaw structure of FIGS. 12A–12B in a second closed position with the slidable extension member moving the jaws to a non-parallel condition so that the distalmost jaw tips engage tissue.
Figure 12D:
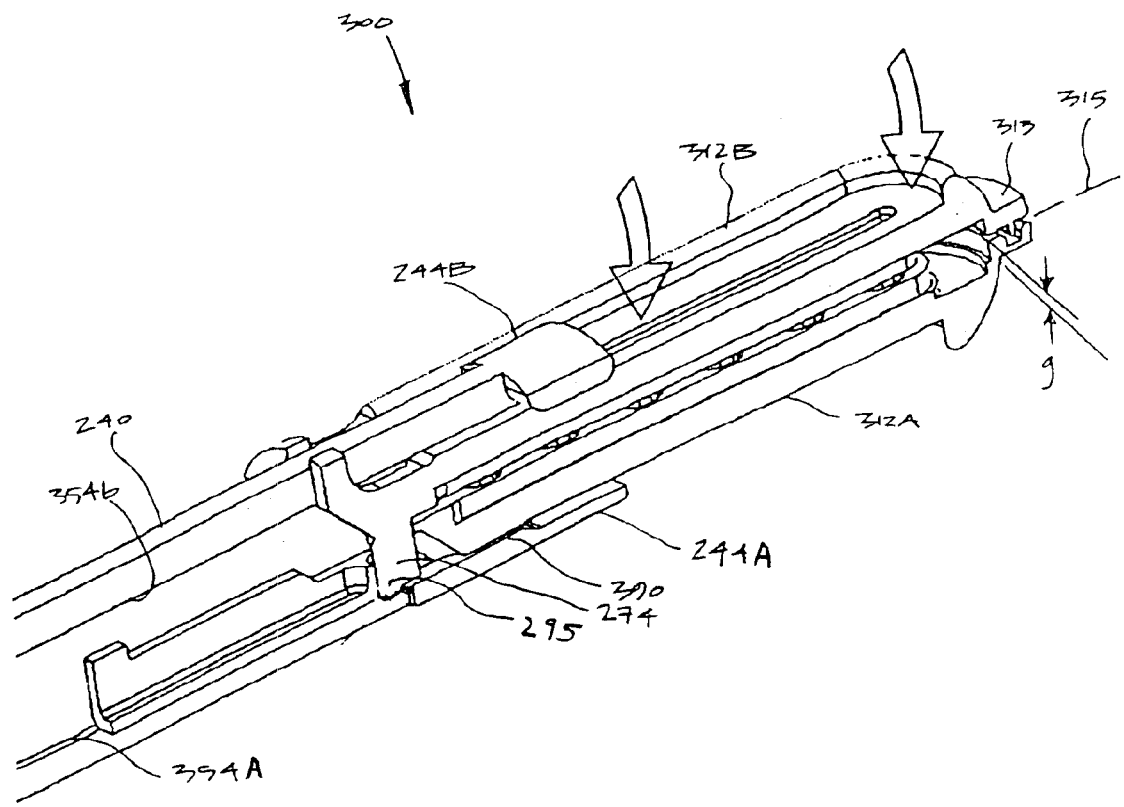
FIG. 12D shows the jaw structure of FIGS. 12A–12C in a third closed position with the slidable extension member moving the jaws to a high-compression parallel condition for tissue welding.
Figure 13:
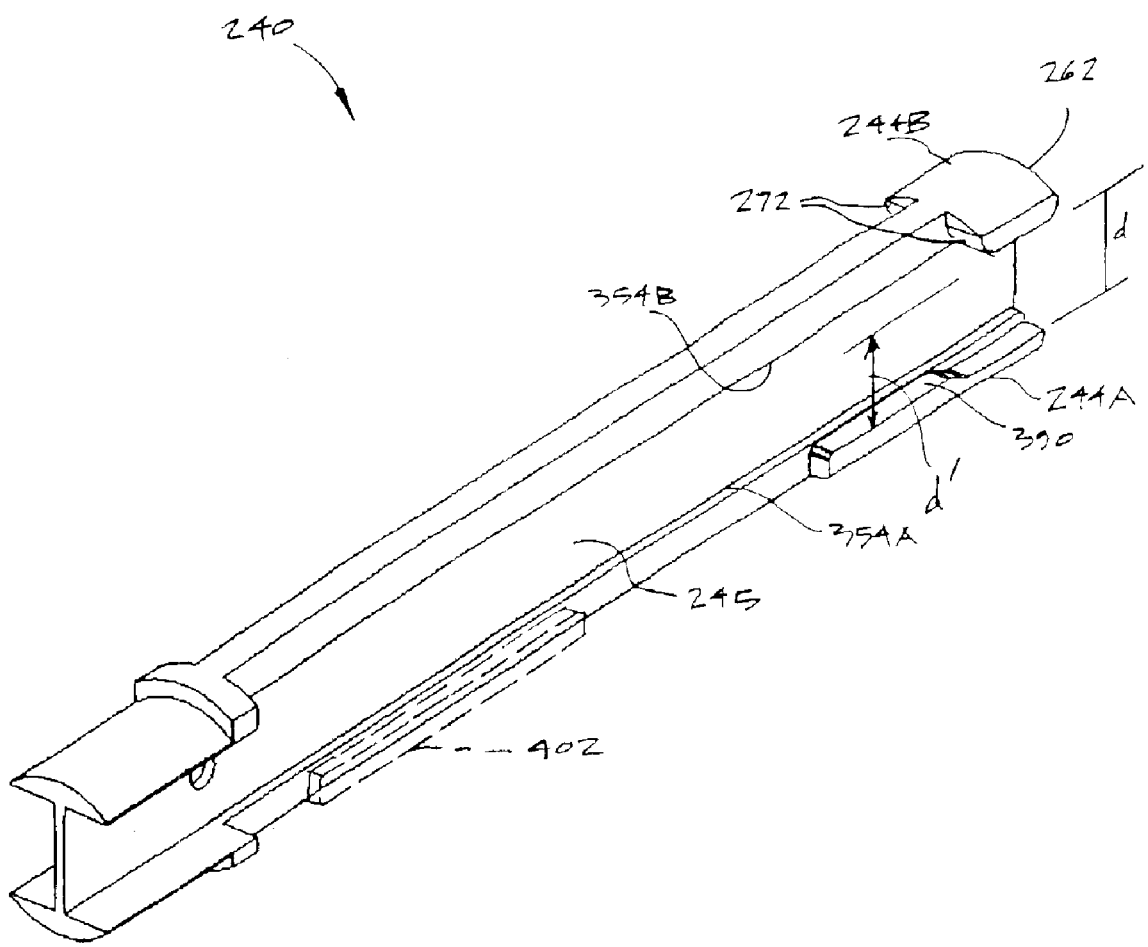
FIG. 13 shows the slidable extension member of FIGS. 12A–12D de-mated from the first and second jaws to show the first and second cam elements.

As can be seen in FIGS. 12A and 13, the lower and upper laterally-extending flange portions 244A and 244B of the reciprocatable member 240 define a transverse dimension d that determines the dimension of gap g between the engagement surface of the jaws in the fully jaw-closed position (FIGS. 10 & 12D). The transverse dimension d equals the dimension between inner surfaces of flange portions 244A and 244B that slidably contact the outer surfaces of both jaws.

FIG. 13 best illustrates that the reciprocatable member 240 is configured with separate elevated step or cam surfaces 390 in the lower flange portions 244A that are adapted to slidably engage the ends 395 of the rectangular pins 274 on either side of upper jaw 312B. The elevated cam surfaces 390 of reciprocatable member 240 thus create another transverse dimension d' between inner surfaces of the flange portions 244A and 244B that move the jaws toward either the first jaw-closed position or the second jaw-closed position.

Now turning to FIGS. 12A–12D, the sequence of cutaway views illustrate how the multiple cam surfaces cause the jaws to move between a first "tilted" jaw-closed position to a second "high-compression" jaw-closed position. In FIG. 12A, the jaws are in an open position. In FIG. 12B, the reciprocatable extension member 240 is moved distally and its cam surface element 262 pushes on jaw surfaces 260 to move the jaws toward a closed position wherein the jaws rotate about primary pivot location $P_1$. In FIG. 12B, it can be seen that the elevated cam surfaces 390 in the lower flange 244A have not yet engaged the ends 295 of the rectangular pins 274.

Now turning to FIG. 12C, the extension member 240 is moved further distally wherein the elevated cam surfaces 390 of lower flange 244A have now engaged and elevated the ends 295 of rectangular pins 274 thereby tilting the upper jaw. The upper jaw 312B is tilted slightly by forces in the direction of the arrows in FIG. 12C as the upper flange 244B holds the upper jaw 312B at a secondary pivoting location indicated at $P_2$—at the same time that the step of the cam surface element 390 lifts the pins 274 and the proximal portion 258 of the upper jaw 312B upward.

Thus, the system functions by providing a slidable cam mechanism for lifting the proximal end of the jaw while maintaining the medial jaw portion in a fixed position to thereby tilt the distal jaw to the second jaw-closed position, with the pivot occurring generally about secondary pivot $P_2$ which is distal from the primary pivot location $P_1$.

FIG. 12D next shows the reciprocatable extension member 240 moved further distally wherein the elevated cam surfaces 390 of lower flange 244A slides distally beyond the ends 295 of rectangular pins 274 thus causing the flanges 244A and 244B together with the trailing edge portions 354A and 354B of the "I"-beam portion (FIG. 13) of the member 240 to apply very high compression forces over the entire length of the jaws as indicated by the arrows in FIG. 12D. This position is termed a parallel jaw-closed position herein. Another advantage of the invention is that the jaw structure is in a "locked" position when the extension member 240 is fully advanced. The instrument does not need a separate mechanism to maintain the jaws locked together as in prior art graspers.

FIG. 13 shows another optional feature of the reciprocatable extension member 240 that is adapted to maintain the proximal end 258 of the jaws in a selected spaced apart position that is substantially parallel. Whereas the upper and lower flange surfaces maintain the engagement surfaces 355A and 355B with a maximum gap therebetween—the flanges do not create a minimum gap which would occur, for example, if tissue were engaged at the distal end of the jaw but not at the proximal end of the jaws. Since the pivot is a "floating-type" pivot, the proximal jaw portion could be pinched together somewhat if tissue was only engaged by the distal jaws when the extension member is in its fully extended position. FIG. 13 shows the extension member 240 with another cam or engagement surface indicated at 402 (phantom view) that is adapted to slide under and engage the ends 295 of the rectangular pins 274 thus cause the proximal jaw portion 258 to have a minimum gap. Thus, the jaws can be maintained with parallel engagement surfaces even with a "floating" pivot. In another embodiment (not shown), the ends 295 of the rectangular pins 274 can be fitted with rollers, bearing or a lubricious coating to insure ease of sliding of the extension member against the ends 295 of the rectangular pins 274.

Although particular embodiments of the present invention have been described above in detail, it will be understood that this description is merely for purposes of illustration. Specific features of the invention are shown in some drawings and not in others, and this is for convenience only and any feature may be combined with another in accordance with the invention. Further variations will be apparent to one skilled in the art in light of this disclosure and are intended to fall within the scope of the appended claims.

What is claimed is:

1. A jaw assembly for a medical device, comprising: an instrument working end that carries openable-closable paired jaws that define first and second pivot locations to thereby provide first and second jaw-closed positions; an elongate jaw defining a first surface portion and a second surface portion for cooperating with moveable cam elements; an axially-moveable extension member carried by the working end, the extension member having a substantially I-beam shape and defining a first cam element for engaging said first surface portion to rotate the jaw about the first pivot location to move the jaws toward the first jaw closed position wherein the jaw faces are substantially parallel; the extension member defining a second cam element for engaging said second surface portion to rotate the jaw about the second pivot location to move the jaws toward the second jaw closed position wherein the jaw faces are non-parallel with approximated distal jaw tips.

2. The jaw assembly of claim 1, wherein the first pivot comprises a floating-type pivot with at least one projecting element that slidably cooperates with at least one bore in the working end.

3. The jaw assembly of claim 1, wherein the paired jaws have channel portions therein for slidably receiving a transverse portion of the extension member.

4. The jaw assembly of claim 1, wherein the extension member has a first upper flange portion that defines said first cam element.

5. The jaw assembly of claim 1, wherein the extension member has a second lower flange portion that defines said second cam element.

6. The jaw assembly of claim 1, further comprising an electrically conductive material in an engagement surface of at least one jaw for receiving electrosurgical energy.

7. The jaw assembly of claim 1, wherein the extension member has a distal blade edge for transecting tissue.

8. The jaw assembly of claim 1, wherein the extension member carries a distal cutting electrode for transecting tissue.

9. A jaw assembly for a medical device, comprising: an instrument working end extending along an axis with an openable-closable jaw structure that provides a first parallel jaw-closed position and a second non-parallel jaw-closed position; an extension member that is axially moveable within the working end between non-extended and extended positions, the extension member having a substantially I-beam shape and defining a first cam element for slidably engaging a first upper surface of a particular jaw and a second cam element for slidably engaging a second lower surface of said particular jaw; wherein movement of the extension member from the non-extended position to a first partially extended position causes the jaws to move toward said first parallel jaw-closed position; and wherein movement of the extension member from said first partially-extended position to a second partially-extended position causes the jaws to move to the second non-parallel jaw-closed position with approximated distal jaw tips.

10. The jaw assembly of claim 9, wherein said first and second cam elements are carried on flange portions of the extension member.

11. The jaw assembly of claim 10, wherein said second lower cam element comprises a step in a said flange portion.

12. The jaw assembly of claim 10 wherein said first cam element is distal to said second cam element relative to the axis of the extension member.

13. A jaw assembly for a medical device, comprising: an instrument working end carrying an openable-closable jaw structure that provides a jaw-open position, a first jaw-closed position and a second jaw-closed position; an extension member that is axially moveable within the working end between non-extended and extended positions, the extension member having a substantially I-beam shape and defining a first cam element for slidably engaging a first jaw surface and a second cam element for slidably engaging a second jaw surface; wherein the extension member in a partially extended position engages said first cam element with said first jaw surface to rotate the jaw structure to said first jaw-closed position; and wherein extension member in an extended position engages said second cam element with said second jaw surface to rotate the jaw structure to said second jaw-closed position in which the distal jaw tips are approximated.

14. The jaw assembly of claim 13, wherein said first cam element is a distal surface of the extension member.

15. The jaw assembly of claim 13, wherein said second cam element is a surface of a flange portion of the extension member.

16. The jaw assembly of claim 13, wherein said second cam element includes a step surface in a flange portion of the extension member.

17. The jaw assembly of claim 13, wherein said first and second jaw surface portions are on respective upper and lower portions of a particular jaw.

18. The jaw assembly of claim 13, wherein the jaw structure defines a central channel for slidably receiving a transverse portion of the extension member.

19. The jaw assembly of claim 13, wherein the extension member carries opposing first and second flange portions that define said first and second cam elements, respectively.

20. The jaw assembly of claim 13, further comprising an electrosurgical conductor in an engagement surface of the jaw structure.

* * * * *